United States Patent [19]

Nordgren et al.

[11] Patent Number: 5,643,297

[45] Date of Patent: Jul. 1, 1997

[54] INTRA-ARTERY OBSTRUCTION CLEARING APPARATUS AND METHODS

[75] Inventors: Gregory N. Nordgren, Wilsonville; Thomas L. Kelly, West Lin, both of Oreg.

[73] Assignee: Endovascular Instruments, Inc., Vancouver, Wash.

[21] Appl. No.: 401,836

[22] Filed: Mar. 10, 1995

Related U.S. Application Data

[62] Division of Ser. No. 973,514, Nov. 9, 1992, abandoned.

[51] Int. Cl.$^6$ ........................................... A61B 17/32
[52] U.S. Cl. ........................ 606/159; 606/170; 606/180; 604/22
[58] Field of Search ........................ 606/159, 170, 606/171, 180; 604/22

[56] References Cited

U.S. PATENT DOCUMENTS

| | | |
|---|---|---|
| 1,167,014 | 1/1916 | O'Brien . |
| 2,505,358 | 4/1950 | Gusberg et al. . |
| 2,541,691 | 2/1951 | Eicher . |
| 2,655,154 | 10/1953 | Richter . |
| 2,701,559 | 2/1955 | Cooper . |
| 2,730,101 | 1/1956 | Hoffman . |
| 2,816,552 | 12/1957 | Hoffman . |
| 2,943,626 | 7/1960 | Dormia . |
| 3,108,593 | 10/1963 | Glassman . |
| 3,108,594 | 10/1963 | Glassman . |
| 3,320,952 | 5/1967 | Wright . |
| 3,320,957 | 5/1967 | Sokolik . |
| 3,334,629 | 8/1967 | Cohn . |
| 3,435,826 | 4/1969 | Fogarty . |

(List continued on next page.)

FOREIGN PATENT DOCUMENTS

| | | |
|---|---|---|
| 9230161 | 9/1992 | European Pat. Off. . |
| 197712 | 12/1977 | U.S.S.R. . |
| 764684 | 9/1980 | U.S.S.R. . |
| 9201054 | 2/1992 | WIPO . |
| 9202222 | 3/1992 | WIPO . |
| WO92/14413 | 3/1992 | WIPO . |
| 93016648 | 9/1993 | WIPO ........................ 606/159 |

OTHER PUBLICATIONS

Reprint from Surgery St. Louis, vol. 57, pp. 22–27, Jan. 1965.

American Edwards Laboratories description sheet for Fogarty Arterial, Emboloectomy Catheters, publication date unknown.

*Primary Examiner*—Guy V. Tucker
*Assistant Examiner*—William Lewis
*Attorney, Agent, or Firm*—Foster & Foster

[57] ABSTRACT

Disposable intra-arterial augering and dottering instruments for use in patients in clearing pathways at obstructed or nearly obstructed arterial sites are disclosed. A number of augering tips used on the instruments are disclosed along with a method for releasibly affixing augering tips to the instruments. In addition, a dottering tip is disclosed for use in procedures where it is desired to open a pathway without excising material from the obstructed site. A combined augering and dottering tip is disclosed for a procedure in which material displacement followed by excising of material from within an artery is accomplished without removal of the combined augering and dottering tip until the procedure is complete.

8 Claims, 9 Drawing Sheets

U.S. PATENT DOCUMENTS

| | | |
|---|---|---|
| 3,467,101 | 9/1969 | Fogarty . |
| 3,467,102 | 9/1969 | Fogarty . |
| 3,472,230 | 10/1969 | Fogarty . |
| 3,509,882 | 5/1970 | Blake . |
| 3,540,431 | 11/1970 | Mobbin-Uddin . |
| 3,704,711 | 12/1972 | Park . |
| 3,811,446 | 5/1974 | Lerwick . |
| 3,952,747 | 4/1976 | Kimmel, Jr. . |
| 3,995,623 | 12/1976 | Blake . |
| 3,996,938 | 12/1976 | Clark, III . |
| 4,020,847 | 5/1977 | Clark, III . |
| 4,030,503 | 6/1977 | Clark, III . |
| 4,046,150 | 9/1977 | Schwartz et al. . |
| 4,207,874 | 6/1980 | Choy . |
| 4,273,128 | 6/1981 | Lary . |
| 4,290,427 | 9/1981 | Chin . |
| 4,315,511 | 2/1982 | Chin . |
| 4,347,846 | 9/1982 | Dormia . |
| 4,425,908 | 1/1984 | Simon . |
| 4,445,509 | 5/1984 | Auth . |
| 4,452,244 | 6/1984 | Chin . |
| 4,494,531 | 1/1985 | Gianturco . |
| 4,559,927 | 12/1985 | Gianturco . |
| 4,574,781 | 3/1986 | Chin . |
| 4,589,412 | 5/1986 | Kensey . |
| 4,592,341 | 6/1986 | Omagari . |
| 4,610,662 | 9/1986 | Wiekl et al. . |
| 4,611,594 | 9/1986 | Grayhack et al. . |
| 4,612,931 | 9/1986 | Dormia . |
| 4,619,246 | 10/1986 | Molgaard-Nielson et al. . |
| 4,621,636 | 11/1986 | Fogarty . |
| 4,625,726 | 12/1986 | Duthoy . |
| 4,630,609 | 12/1986 | Chin . |
| 4,631,052 | 12/1986 | Kensey . |
| 4,643,184 | 2/1987 | Mobbin-Uddin . |
| 4,648,402 | 3/1987 | Santos . |
| 4,650,466 | 3/1987 | Luther . |
| 4,653,496 | 3/1987 | Bundy et al. . |
| 4,655,217 | 4/1987 | Reed . |
| 4,669,464 | 6/1987 | Sulepov . |
| 4,681,106 | 7/1987 | Kensey et al. . |
| 4,682,599 | 7/1987 | Konomura . |
| 4,688,553 | 8/1987 | Metals . |
| 4,692,139 | 9/1987 | Stiles . |
| 4,696,667 | 9/1987 | Masch . |
| 4,699,147 | 10/1987 | Chilson et al. . |
| 4,699,469 | 10/1987 | Gifford . |
| 4,706,671 | 11/1987 | Weinrib . |
| 4,721,507 | 1/1988 | Chin . |
| 4,723,549 | 2/1988 | Wholley et al. . |
| 4,727,873 | 3/1988 | Mobbin-Uddin . |
| 4,732,154 | 3/1988 | Shiber . |
| 4,739,760 | 4/1988 | Chin et al. . |
| 4,745,919 | 5/1988 | Bundy . |
| 4,755,175 | 7/1988 | Nilsson . |
| 4,762,130 | 8/1988 | Fogarty . |
| 4,765,332 | 8/1988 | Fischell . |
| 4,768,505 | 9/1988 | Okada . |
| 4,768,508 | 9/1988 | Chin et al. . |
| 4,781,177 | 11/1988 | Lebigot . |
| 4,790,812 | 12/1988 | Hawkins, Jr. et al. . |
| 4,793,348 | 12/1988 | Palmaz . |
| 4,807,626 | 2/1989 | McGirr . |
| 4,808,163 | 2/1989 | Laub . |
| 4,819,634 | 4/1989 | Shiber . |
| 4,820,283 | 4/1989 | Schinkling et al. . |
| 4,820,349 | 4/1989 | Saab . |
| 4,832,055 | 5/1989 | Palestrant . |
| 4,842,579 | 6/1989 | Shiber . |
| 4,850,957 | 7/1989 | Summers . |
| 4,857,045 | 8/1989 | Rydell . |
| 4,867,156 | 9/1989 | Stack . |
| 4,871,613 | 10/1989 | Jaraczewski et al. . |
| 4,873,978 | 10/1989 | Ginsberg . |
| 4,886,061 | 12/1989 | Fischell . |
| 4,886,490 | 12/1989 | Shiber . |
| 4,887,613 | 12/1989 | Farr et al. . |
| 4,890,611 | 1/1990 | Monfort et al. . |
| 4,892,099 | 1/1990 | Ohkawa et al. . |
| 4,892,519 | 1/1990 | Songer et al. . |
| 4,894,051 | 1/1990 | Shiber . |
| 4,895,166 | 1/1990 | Farr et al. . |
| 4,895,560 | 1/1990 | Papantonakos . |
| 4,898,575 | 2/1990 | Fischell . |
| 4,905,689 | 3/1990 | Stack et al. . |
| 4,909,781 | 3/1990 | Husted . |
| 4,913,704 | 4/1990 | Kurimoto . |
| 4,917,085 | 4/1990 | Smith . |
| 4,917,102 | 4/1990 | Miller . |
| 4,921,478 | 5/1990 | Solano et al. . |
| 4,921,482 | 5/1990 | Hammserslag et al. . |
| 4,921,483 | 5/1990 | Wijay et al. . |
| 4,921,484 | 5/1990 | Hillstead . |
| 4,923,462 | 5/1990 | Stevens . |
| 4,926,858 | 5/1990 | Gifford, III et al. . |
| 4,943,297 | 7/1990 | Saveliev et al. . |
| 4,957,482 | 9/1990 | Shiber . |
| 4,966,604 | 10/1990 | Reiss . |
| 4,979,939 | 12/1990 | Shiber . |
| 4,986,807 | 1/1991 | Farr . |
| 4,994,067 | 2/1991 | Summers . |
| 5,002,553 | 3/1991 | Shiber . |
| 5,007,896 | 4/1991 | Shiber . |
| 5,009,659 | 4/1991 | Hamlin et al. . |
| 5,019,088 | 5/1991 | Farr . |
| 5,019,089 | 5/1991 | Farr . |
| 5,024,651 | 6/1991 | Shiber . |
| 5,026,384 | 6/1991 | Farr et al. . |
| 5,030,201 | 7/1991 | Palestrant . |
| 5,041,082 | 8/1991 | Shiber . |
| 5,041,089 | 8/1991 | Mueller et al. . |
| 5,047,040 | 9/1991 | Simpson et al. . |
| 5,047,041 | 9/1991 | Samuels . |
| 5,053,008 | 10/1991 | Bajaj . |
| 5,053,044 | 10/1991 | Mueller et al. . |
| 5,055,109 | 10/1991 | Gould et al. . |
| 5,057,092 | 10/1991 | Webster, Jr. . |
| 5,057,114 | 10/1991 | Wittich et al. . |
| 5,071,424 | 12/1991 | Reger . |
| 5,074,841 | 12/1991 | Ademovic et al. . |
| 5,074,871 | 12/1991 | Groshong . |
| 5,078,722 | 1/1992 | Stevens . |
| 5,078,723 | 1/1992 | Dance et al. . |
| 5,084,010 | 1/1992 | Plaia et al. . |
| 5,085,662 | 2/1992 | Willard . |
| 5,087,256 | 2/1992 | Taylor et al. . |
| 5,087,265 | 2/1992 | Summers . |
| 5,100,424 | 3/1992 | Jang et al. . |
| 5,100,425 | 3/1992 | Fischell . |
| 5,100,426 | 3/1992 | Nixon . |
| 5,102,415 | 4/1992 | Guenther et al. . |
| 5,104,399 | 4/1992 | Lazarus . |
| 5,108,411 | 4/1992 | McKenzie . |
| 5,108,414 | 4/1992 | Enderle et al. . |
| 5,112,325 | 5/1992 | Zachry . |
| 5,112,345 | 5/1992 | Farr . |
| 5,114,399 | 5/1992 | Koulcheck . |
| 5,114,423 | 5/1992 | Kaspryzk et al. . |
| 5,127,902 | 7/1992 | Fischell . |
| 5,127,917 | 7/1992 | Niederhauser et al. . |
| 5,133,733 | 7/1992 | Rasmussen et al. . |
| 5,135,482 | 8/1992 | Neracher . |

| | | |
|---|---|---|
| 5,135,483 | 8/1992 | Wagner et al. . |
| 5,135,484 | 8/1992 | Wright . |
| 5,135,531 | 8/1992 | Shiber . |
| 5,152,773 | 10/1992 | Redha . |
| 5,154,724 | 10/1992 | Andrews . |
| 5,192,292 | 3/1993 | Cezana et al. . |
| 5,224,945 | 7/1993 | Pannek, Jr. . |
| 5,226,909 | 7/1993 | Evans et al. . |
| 5,242,460 | 9/1993 | Klein et al. . |
| 5,242,461 | 9/1993 | Kortenbach et al. . |
| 5,250,059 | 10/1993 | Andreas et al. . |
| 5,261,877 | 11/1993 | Fine et al. . |
| 5,267,955 | 12/1993 | Hanson . |
| 5,304,115 | 4/1994 | Pflueger et al. . |
| 5,409,454 | 4/1995 | Fischell et al. . |
| 5,423,799 | 6/1995 | Shiu .......... 606/159 |
| 5,512,044 | 4/1996 | Duer .......... 606/159 |

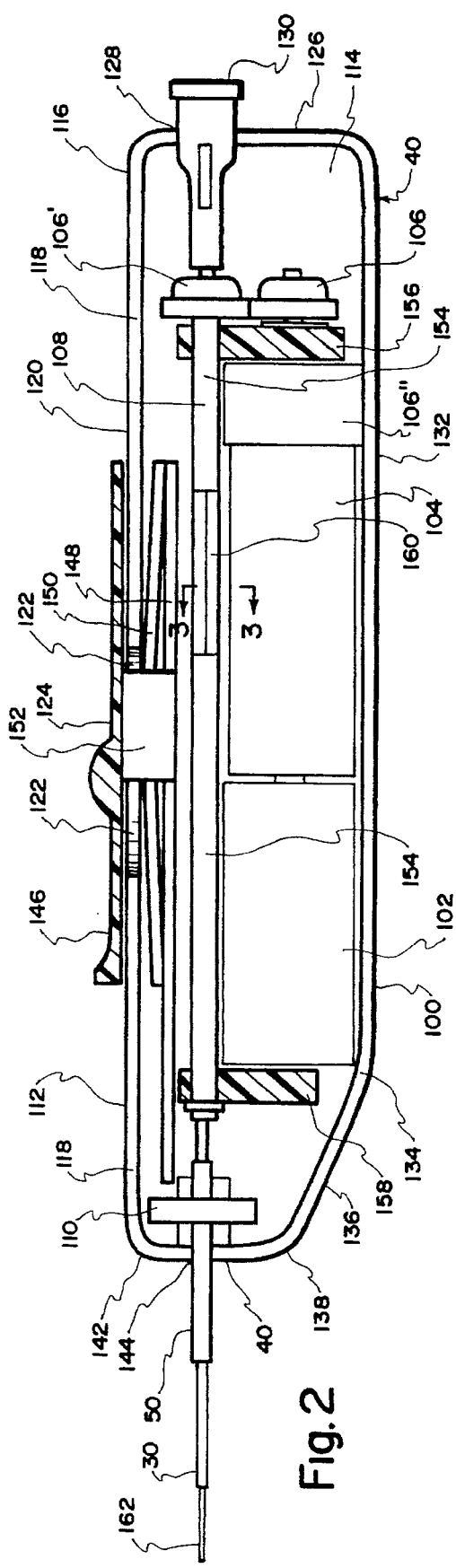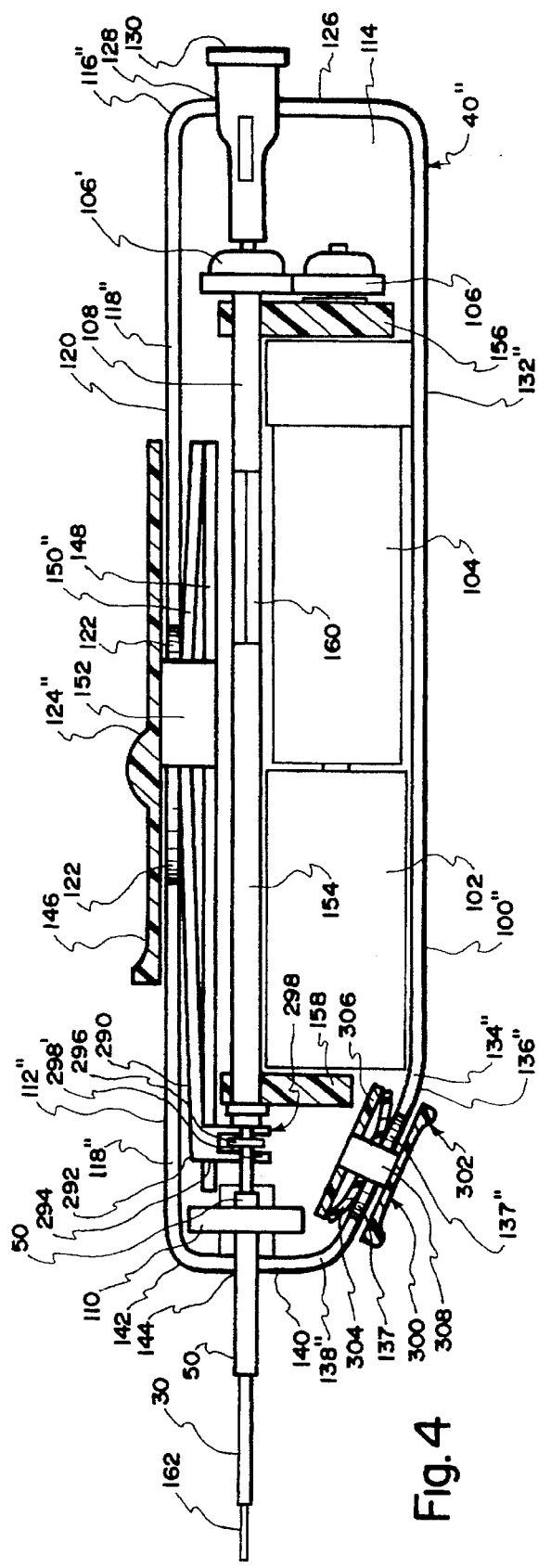

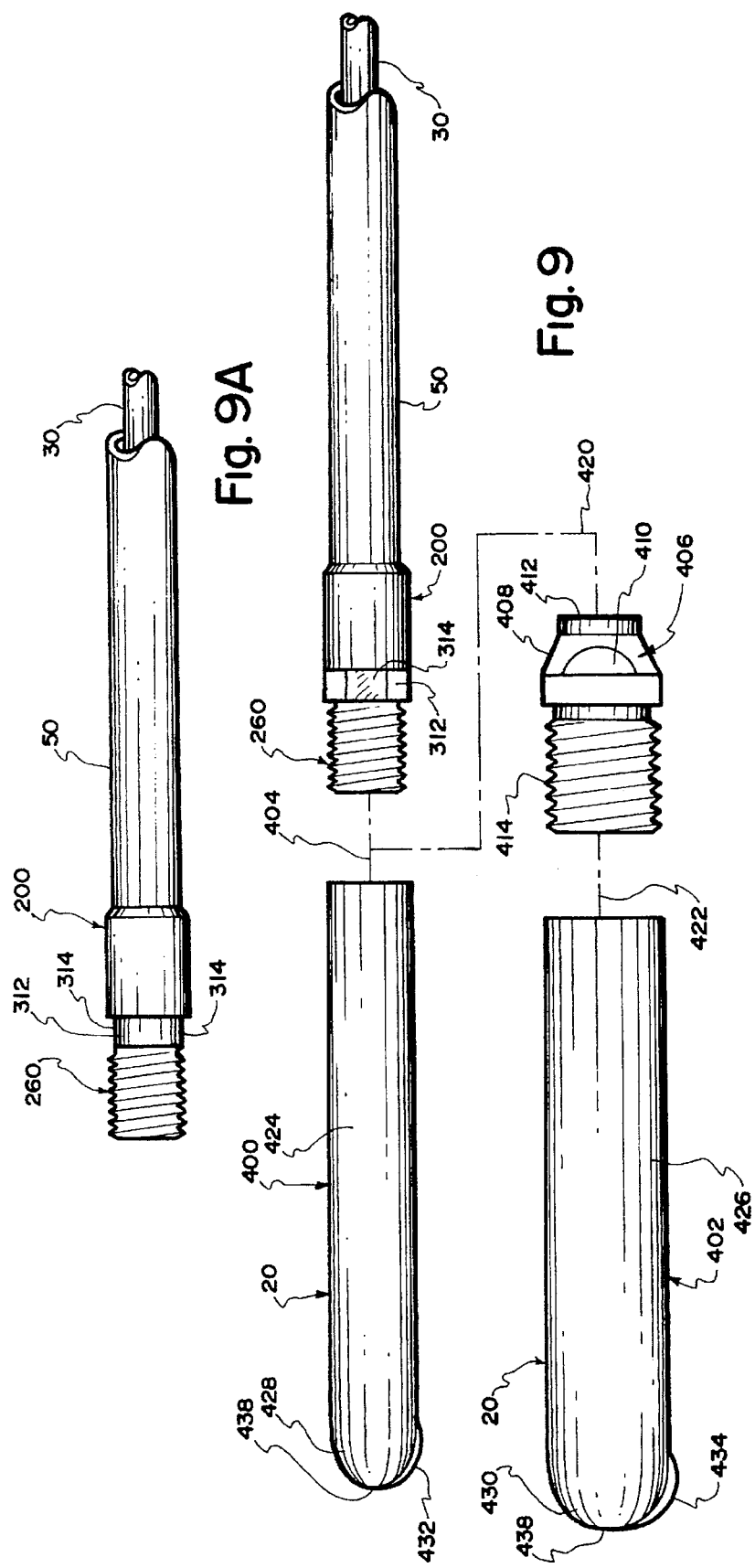

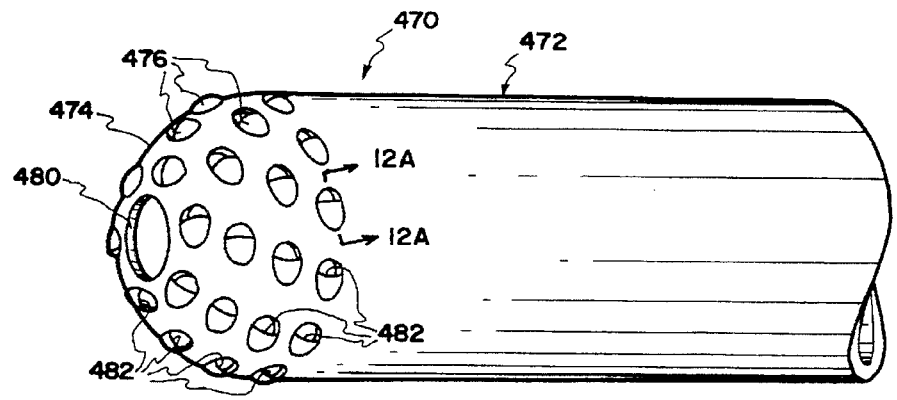
Fig. 12
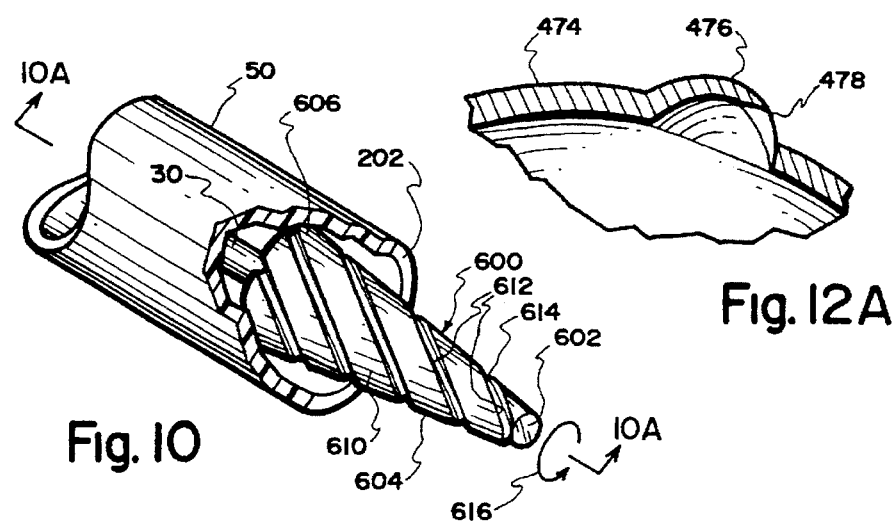
Fig. 10
Fig. 12A
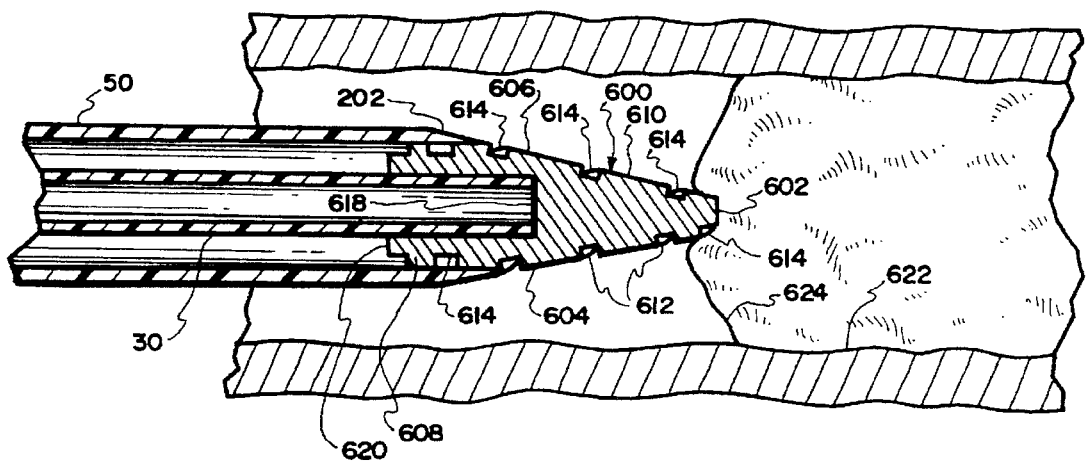
Fig. 10A

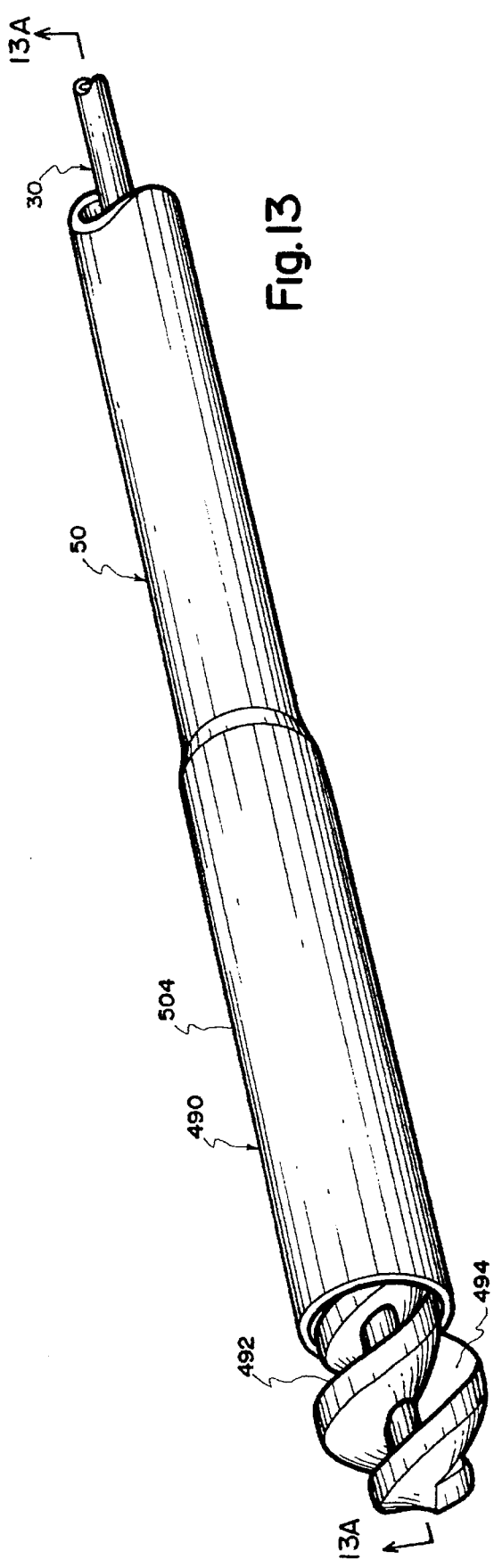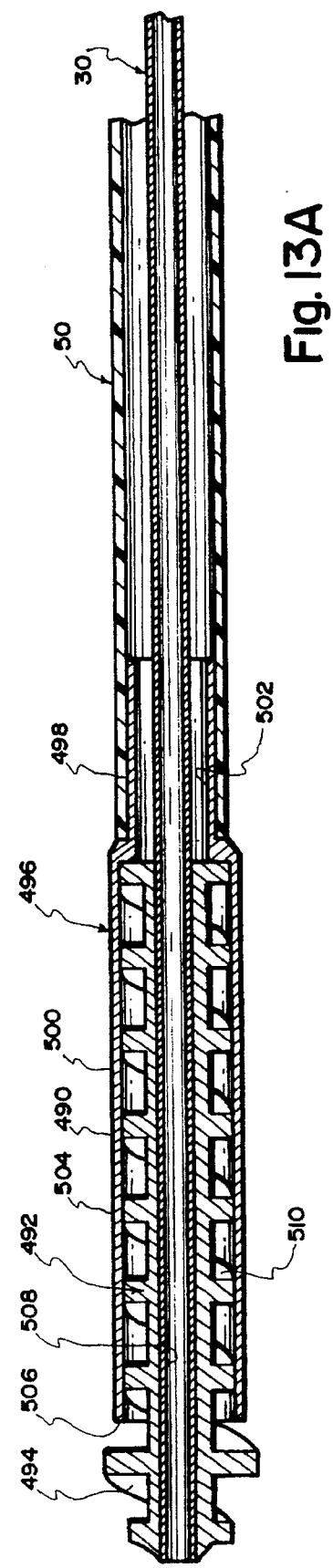

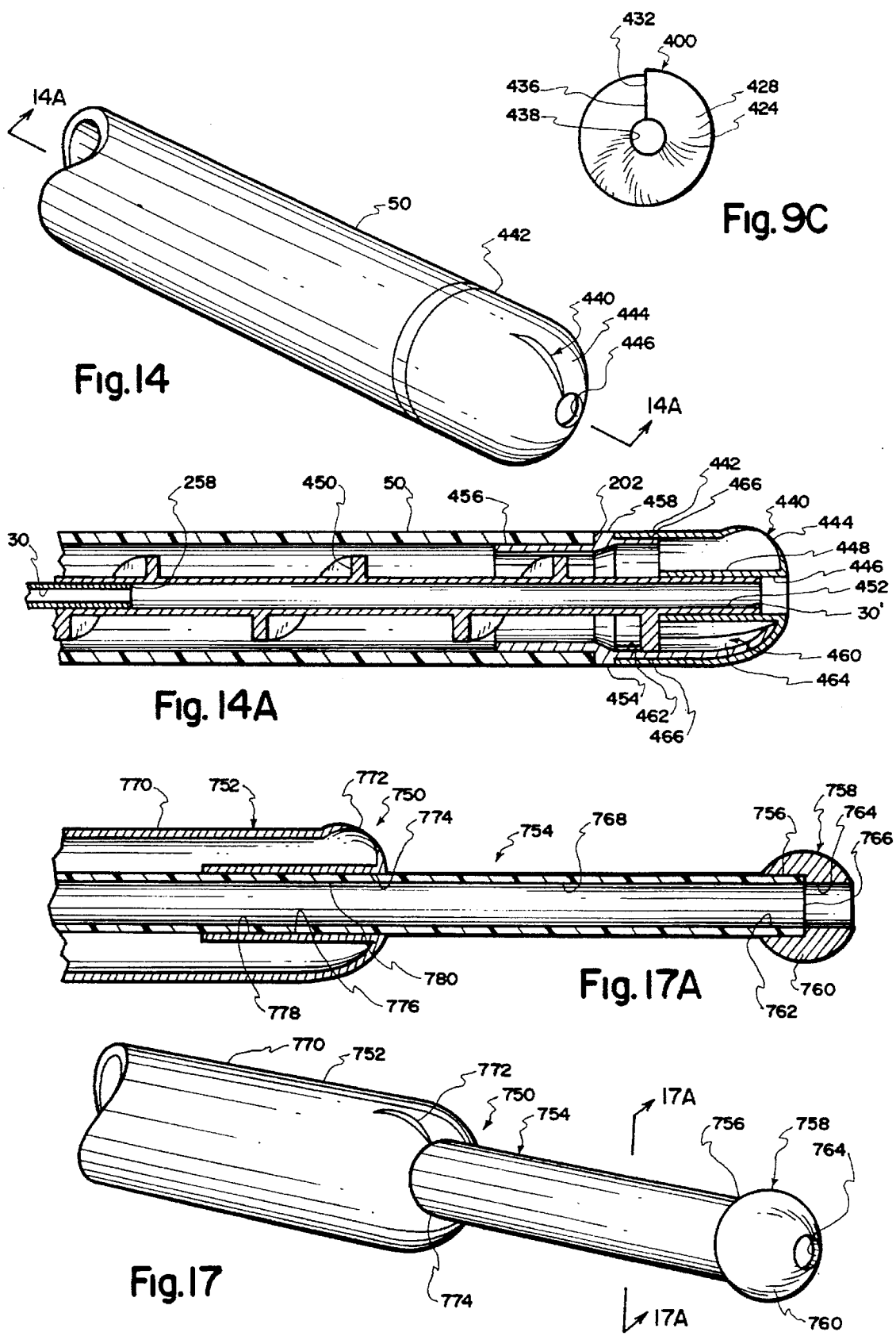

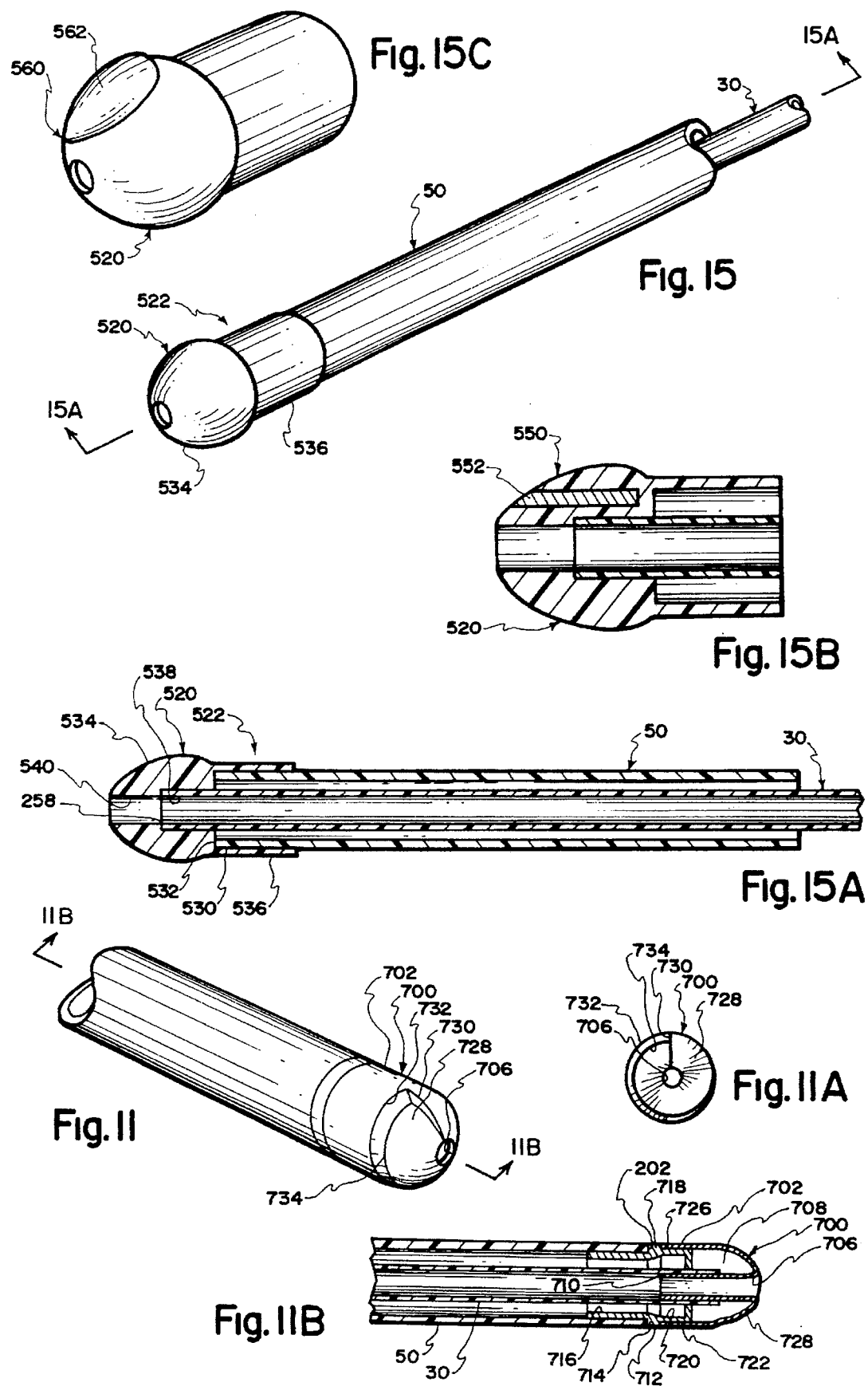

INTRA-ARTERY OBSTRUCTION CLEARING APPARATUS AND METHODS

This application is a division of my U.S. patent application Ser. No. 07/973,514, filed Nov. 9, 1992, now abandoned.

FIELD OF THE INVENTION

This invention relates to apparatus and methods used in endarterectomy and more particularly to atherectomy or augering or obstructive material displacement apparatus and methods involved in partial removal of a blood vessel obstructing or nearly obstructing atheroma to clear a pathway through the obstruction for other subsequently utilized atherectomy or endarterectomy devices employed for more complete removal of the atheroma.

BACKGROUND AND DESCRIPTION OF RELATED ART

With the advent of endovascular coring and collecting catheters, the helical cutting catheter and filtration tip endovascular guide wire, it is possible not only to open but to remove all atheroma from a defined length of partially occluded arteries with minimal risk of downstream embolization. Furthermore, this can be carried out through a single entry point in the artery, as compared to earlier techniques using the Hall Loop or Cannon Dissector, both of which require two points of entry.

Apparatus and methods, such as those disclosed in U.S. Pat. Nos. 5,071,424 and 5,074,871 are used to perform near total removal of an atheroma. However, when treating atheroma such as in lower limb ischemia in the superficial femoral artery, occlusions are sometimes complete or nearly complete making use of presently available endarterectomy apparatus in removal of the atheroma very difficult, if not impossible. Otherwise useful presently available endarterectomy devices require at least a portion of the device to be positioned through and distal to the atheroma before excision can begin. When stenosis of a vessel is so bad that operation of the presently available endarterectomy devices is prohibited due to severe obstructive stenosis, the vessel must be at least partially opened to provide a pathway before the other endarterectomy devices can be efficaciously used.

One of the critical problems which must be addressed when clearing a pathway in a completely or nearly completely obstructed artery is binding of a cutting tip or associated sleeves and catheters within the obstruction. Another problem is clearing a pathway without excising material from the atheroma under circumstances where recovery of excised particles is difficult. Still another problem deals with a need to exchange cutting tips as a need for different pathway diameters and various hardnesses of tissue are encountered during the opening of a pathway. One further important problem is providing a clean, sterile instrument for each procedure. Parts used to clear obstructive tissue from arteries involve extremely small and intricate parts into which excised particles are often captured for recovery from an excised site. Appropriate safe and efficacious cleaning and sterilization of used instruments for reuse is usually impractical, if not impossible.

BRIEF SUMMARY AND OBJECTS OF THE INVENTION

In brief summary, this novel invention alleviates known problems associated with establishing a pathway through an occluded or partially occluded arterial atheroma site. The invention is used to efficaciously and safely create a pathway through an occluded or partially occluded atheroma site thereby creating a pathway for passage of endarterectomy devices subsequently used to more completely remove the atheroma from the interior arterial wall.

This invention is particularly well suited to breaching stenotic sites in vessels where atheroma removal is unable to be addressed by currently available endarterectomy devices. Thus, the use of this invention permits follow-on use of endarterectomy devices in vessels initially untreatable by the currently available endarterectomy devices alone. Used in combination with the above mentioned endarterectomy devices, this invention plays a principle role in safely and efficaciously opening critically stenotic vessels.

The invention comprises a totally disposable instrument packaged into a sterility maintaining package such that no pre-use sterilization or post-use sterilization is required of an end user. The instrument comprises removable and replaceable cutting tips allowing a variable response to unpredictable problems encountered when clearing a pathway through an obstructed artery.

In a first embodiment of a cutting tip, this invention comprises a material removing and retrieving part contained within the cutting tip. In a second embodiment, this invention comprises a material displacing tip. The displacing tip is distally disposed at an inserted end of the catheter and compacts or otherwise displaces material at a stenotic site to clear a pathway for blood and a subsequently used guidewire, balloon catheter or atherectomy device.

This invention is also to be used as a precursor to transluminal balloon dilation and other devices which require at least a limited diametral opening past the atheroma or stenotic site.

Accordingly, it is a primary object to provide a disposable augering and coring instrument with a variety of selectable obstructed pathway opening tips.

It is another primary object to provide a disposable augering and dottering device and catheter combination which is used only during a procedure on a single patient and then thrown away.

It is an object to provide a device used in combination with a catheter to core, auger, or dotter its way through a partially or fully blocked body canal or blood vessel, such as a severely stenotic artery.

It is yet another primary object to provide a device used in combination with a catheter to create a pathway through a stenotic site preparatory to using other endarterectomy devices which cannot transverse a tight stenosis, but which are efficaciously used for completely opening the canal or blood vessel once the pathway is available, the pathway having a transverse diameter sufficient to pass the other endarterectomy devices and, alternatively, to permit flow of blood through the site of the stenosis.

It is a principal object to provide a device used in combination with a catheter having flexibility to track along a canal or blood vessel and to remove plaque and other objects encountered in the canal or blood vessel without injuring normal tissue found at the interface between the canal or blood vessel lumen and the internal canal or blood vessel wall surface.

It is another principal object to provide an instrument having a plurality of pathway clearing tips and used in combination with a catheter to remove a variety of materials ranging from an extremely hard calcified plaque to soft and fibrous atheroma or scar tissue without harm to the canal or blood vessel wall.

It is an important object to provide a device used in combination with a catheter to collect and retrieve substantially all material excised from the lumen of the canal or blood vessel by the device.

It is still another object to provide a device used in combination with a catheter to create a pathway through a stenotic site by displacing rather than removing material.

It is yet another object to provide a device used in combination with a catheter which displaces material by spinning or vibrating or by spinning and vibrating to create a pathway for other endarterectomy material removing devices.

It is an object to provide a device used in combination with a catheter to track along a guide wire within the canal or blood vessel to the stenotic site.

These and other objects and features of the present invention will be apparent from the detailed description taken with reference to accompanying drawings.

BRIEF DESCRIPTION OF THE DRAWINGS

FIG. 2 is a section along lines 2—2 of FIG. 1.

FIG. 4 is a section similar to the section of FIG. 2, but of a different embodiment than that of FIG. 2.

FIG. 9 is an exploded view of parts adapted to connect to the cable driver adapter.

FIG. 9A is a part comprising the cable driver adapter rotated 90° relative to the same part in FIG. 9.

FIG. 9B is a side view of the tip diameter adjusting connector rotated 90° relative to the tip diameter adjusting connector seen in FIG. 9.

FIG. 9C is an end view of the tip of FIG. 7.

FIG. 10 is a perspective of a conical augering tip partially disposed in the lumen of a catheter.

FIG. 10A is a section along lines 10A—10A of FIG. 10 with the conical augering tip disposed for cutting inside an artery having a partially prepared pathway cut through an obstructive atheroma at the site of the conical augering tip.

FIG. 11 is a perspective of a spirally configured cutting tip and associated section of a catheter.

FIG. 11A is and end view of the cutting tip of FIG. 11.

FIG. 11B is a section along lines 11B—11B of FIG. 11.

FIG. 12 is a perspective of an end portion of a tip comprising a plurality of grater type cutting edges.

FIG. 12A is an enlarged section along lines 12A—12A of FIG. 12.

FIG. 13 is a perspective comprising a screw type tip.

FIG. 13A is a section along lines 13A—13A of FIG. 13.

FIG. 14 is a perspective comprising a self-clearing tip.

FIG. 14A is a section along lines 14A—14A of FIG. 14.

FIG. 15 is a perspective of a dottering tip mounted on the distal end of a catheter.

FIG. 15A is a section taken along lines 15A—15A of FIG. 15.

FIG. 15B is a dottering tip similar to the tip of FIG. 15, but comprising an asymmetrically weighted section.

FIG. 15C is a dottering tip similar to the tip of FIG. 15, but comprising an asymmetrical bulge on one side of the dottering tip.

FIG. 17 is a perspective of a combined augering and dottering tip.

FIG. 17A is a cross section along lines 17A—17A of FIG. 17.

DETAILED DESCRIPTION OF THE ILLUSTRATED EMBODIMENTS

In this description, the term proximal is used to indicate the segment of the device normally closest to an administerer or user of the device. The term distal refers to the other end. The term dotter refers to a side to side oscillation, such as an oscillation transverse to the longitudinal axis of a catheter. Reference is now made to the embodiments illustrated in FIGS. 1–16 wherein like numerals are used to designate like parts throughout.

Figure 1:
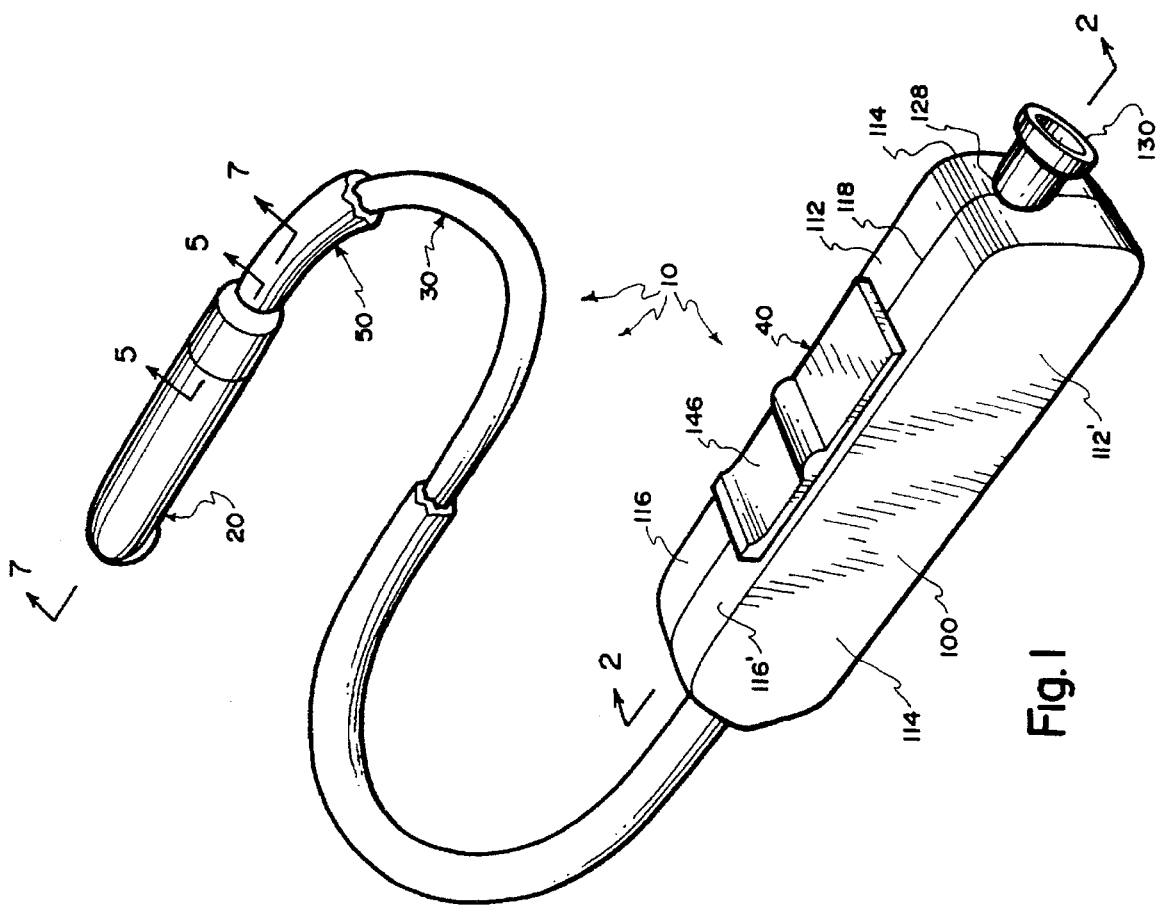
FIG. 1 is a perspective of a disposable intra-artery pathway clearing device.

One embodiment of this invention, seen in FIG. 1, comprises a disposable mechanized instrument 10 which is used during an atherectomy procedure on but one patient and thrown away thereafter. To provide efficacious service for both patient and administerer, instrument 10 is sufficiently low in replacement cost that consideration of cleaning and sterilization is not an economic factor. Also, power supplying parts and other mechanical parts have a sufficiently long shelf life to permit use on an intermittent, on-call basis directly from storage over an extended periods, such as a period of two to five years.

Instrument 10 comprises an augering or dottering tip, generally designated 20, a hollow drive cable 30, mechanically attached to rotate tip 20, a handle 40 enclosing parts by which drive cable 30 is driven, and a catheter 50 interposed between tip 20 and handle 40 to enclose drive cable 30 therebetween. In use, tip 20 and catheter 50 of instrument 10 are inserted into an artery of a patient and delivered to the site where an artery is obstructed or at least so obstructed that other atherectomy devices, including a guide wire 162 (see FIGS. 2 and 4), are unable to traverse the site. One of the primary purposes of augering or dottering tip 20 is to provide a pathway for guide wire 162 through an obstruction. On other occasions, guide wire 162 may be used as a guide for travel of tip 20 and catheter 50 within the artery.

Once delivered to the site of the obstruction, tip 20 is actuated via drive cable 30 to open a pathway through the atheroma for increased blood flow and passage of other atheroma removing instruments which could not be used effectively until the pathway was opened. An important consideration in the selection and use of a tip 20 is production of a pathway through the obstruction in which tip 20 or catheter 50 does not bind and become lodged. The pathway cleared through the atheroma, therefore, comprises a sufficiently large cross section for tip 20 and catheter 50 when delivered therethrough and for a subsequently used other atherectomy device used to completely clear atheroma from the site.

A more detailed view of handle 40 and parts packaged in handle 40 is seen in FIG. 2. Handle 40 comprises a housing 100 molded to enclose a battery 102, a motor 104, gears 106, 106', and gearhead 106" which interface the motor to a drive cable drive channel 108, and a mounting bracket 110 used to permanently and rigidly affix catheter 50 to the handle. Housing 100 is made from rigid synthetic resinous material which is able to withstand sterilization procedures, such as gas or radiation sterilization.

Housing 100 comprises a pair of mounting shells 112 and 112', best seen in FIG. 1, mounting shell 112' being a mirror image of mounting shell 112. For this reason, only details of mounting shell 112 will be provided herein. In final assembly, mounting shell 112 is permanently joined to mounting shell 112' by chemical, heat, ultrasound or other bonding techniques well known in the art to provide a durable, throw-away unit. Shells 112 and 112' may be formed by injection molding or vacuum forming techniques well known in the art.

As seen in FIGS. 1 and 2, housing 100 provides a shape compatible for gripping with a single hand. Shell 112 comprises an enclosing side 114 orthogonally connected to a continuous perimeter 116 which surrounds half the space between side 114 and a side 114' on shell 112' when shells 112 and 112' are engaged. Shell 112' comprises a perimeter 116', which is a mirror image of perimeter 116 and which encloses the other half of the space between side 114 and side 114'.

A substantially planar rim 118 is disposed parallel to side 114 but on a side of perimeter 116 opposite side 114. Perimeter 116 comprises a longest edge 120 which extends substantially along the length of handle 40 and is intended to provide a superiorly disposed thumb rest while in use. Medially disposed in edge 120 is a depression or recess 122 wherethrough a slidable mechanical device 124 is captured. The purpose for and function of device 124 is described in detail hereafter.

Disposed at a right angle to edge 120 is a proximal edge 126. A semicircular slot 128 in combination with a similar slot in perimeter 116' provides access for a luer fitting 130, the purpose of which is described hereafter. Inferiorly disposed and extending parallel to edge 120 from edge 126 is edge 132. Edge 132 extends in a straight line from edge 126 to a bend 134, although it is within the scope of the invention to provide scallops or grooves in edge 132 for more positive finger gripping of handle 40. At bend 134, edge 132 bends to form a bevelled edge segment 136 which may act as a rest or gripping surface for a forefinger.

At a bend 138, segment 136 is joined an edge 140 which is orthogonally joined at bend 142 with edge 120 to complete perimeter 116. Medially disposed along a line which is parallel to edge 120 and which bisects slot 128, a catheter 50 exit slot 144 is disposed in edge 140. Additional detail regarding catheter 50 attachment and alignment is provide hereinafter.

As seen in FIG. 2, device 124 comprises an actuator 146 positioned to be normally operated by a thumb, a support bar 148, a memory biased member 150, and a coupling member 152. Member 152 is affixed to actuator 146 and captures support bar 148 and bias member 150 such that edge 120 is disposed between actuator 146 and bias member 150. Further, member 152 slides within a slot formed in part by recess 122 and a like recess in perimeter 116' between at least a first proximal position and a second distal position. In the embodiment seen in FIG. 2, bias member 150 is spring loaded to bias bias member 150 and support bar 148 away from edge 120 and comprises an electrical contactor (not shown) which makes an electrical contact with another contactor disposed on a medial side of edge 120 (also not shown) only at the second distal position. The electrical contacts and other electrical wiring is not shown in FIG. 2 as such is well known in the art and has been removed to provide greater detail and clarity of mechanical parts of handle 40.

Within handle 40, a cable drive system comprises device 124, battery 102, motor 104, gears 106 and 106', and cable drive channel 108. Battery 102 and motor 104 are aligned along edge 132 and confined by edge 132, sides 114 and 114', and brackets molded or formed into sides 114 and 114', the molded or formed brackets are not shown but molding and forming such brackets is widely practiced and well known in handle molding art.

Rotary motor power is transferred through gear 106 to gear 106' and therefrom to cable drive channel 108. Cable drive channel 108 comprises a round hollow tube 154 captured in grooves in bearing parts 156 and 158 and like shell 112' parts disposed at each end of cable drive channel 108. Medially disposed between bearing parts 156 and 158, tube 154 is squared by compressive techniques known in the art to form a cross sectionally square segment 160. Cable drive channel 108 is centrally aligned with luer fitting 130, gear 106', and catheter 50 mounting bracket 110. This alignment permits drive cable 30 to be interconnected with cable drive channel 108 and threaded through catheter 50 such that drive cable 30 rotates without binding within catheter 50. Further guide wire 162 is threadable end-to-end through hollow drive cable 30, entering handle 40 through luer fitting 130.

Figure 3:
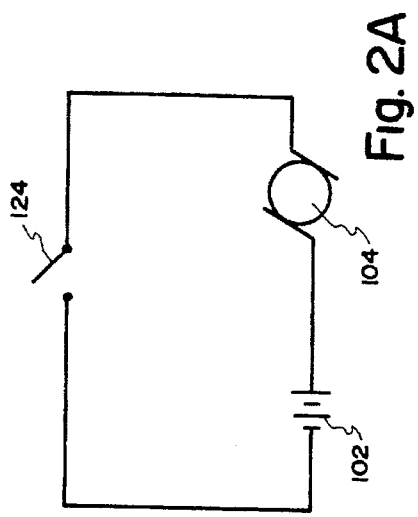
FIG. 3 is a section along lines 3—3 of FIG. 2.

A section taken across segment 160 is seen in FIG. 3. As seen in FIG. 3, a section 164 of square channel material having a diagonal dimension which is smaller than the internal diameter of tube 154, but larger than internal side dimensions of segment 160 is bonded or otherwise permanently affixed to the proximal end of drive cable 30. A portion of drive cable 30 comprising section 164 is disposed into segment 160 such that at least a portion of section 164 is retained in segment 160 during all operational modes of instrument 10. As such drive cable 30 is rotationally driven as cable drive channel 108 is rotated by action of motor 104 through gears 106 and 106'. However, drive cable 30 is free to move longitudinally within cable drive channel 108 and, therefore, within catheter 50 as catheter 50 is moved through an artery to eliminate binding of drive cable 30 as catheter 50 moves differentially relative to drive cable 30. Drive cable 30 is retained inside catheter 50 and segment 160 by a stop disposed near the distal end of catheter 50 as is described hereafter.

Cable drive channel 108 may be made of a malleable metal such as steel or aluminum. Section 164 may be made from a rigid synthetic resinous material or metal which is readily bonded or otherwise affixed to drive cable 30. A wide range of motors may be used within the scope of the invention. As currently preferred, Motor 104 may be a Maxon Precision Motor number 2515.980-61.111-000.

Gears having a wide range of teeth and ratios may also be used. As currently preferred, Gear head 106" may be provided as Maxon Precision Motor Gearhead number 1916.803-0013-000. In the currently preferred embodiment ninety-six-pitch gears are employed, as such a 38:38 tooth ratio provides an output rotational speed of drive cable 30 of approximately 660 revolutions per minute, a 42:35 tooth ratio provides an output rotational speed of drive cable 30 of approximately 780 revolutions per minute, and a 35:42 tooth ration provides an output rotational speed of drive cable 30 of approximately 550 revolutions per minute, although other gears and gear ratios may be used within the scope of the invention. A long shelf-life lithium three volt Lithium battery warranted for a period of five years and commercially available may be used as battery 102 to provide off-the-shelf power for motor 104.

Figure 2A:
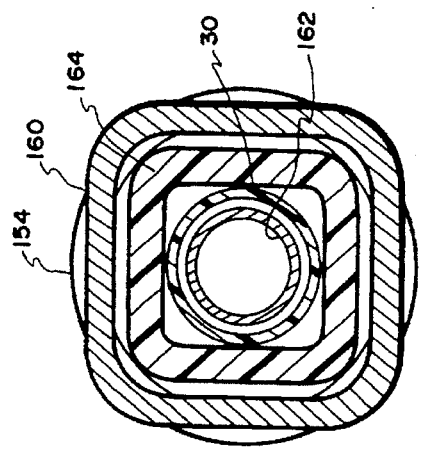
FIG. 2A is a circuit diagram comprising a power control switch, a battery and a motor.

As seen in FIG. 2A, motor 104 is activated when actuator 146 is moved distally to close a contact associated with device 124 and provide batter 102 power to the motor 104. Conversely power is removed from motor 104 by moving actuator 146 proximally to break the contactor associated with device 124.

Figure 5:
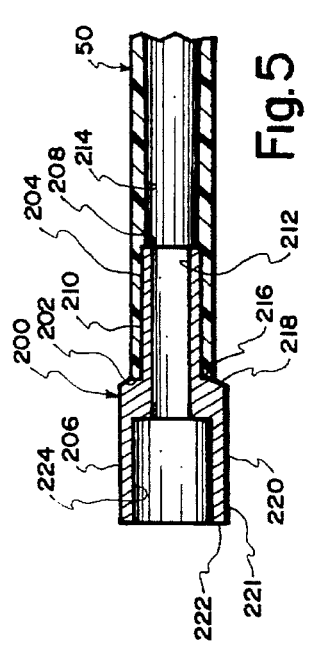
FIG. 5 is a section of a catheter end attachment taken along lines 5—5 of FIG. 1.

To provide a cutting tip 20 interface, an adapter 200 is attached to a blunt distal end 202 of catheter 50 as seen in FIG. 5. Adapter 200 may be metal or a rigid synthetic resinous material which preferably comprises a self-lubricating surface. Generally, adapter 200 comprises a catheter insertion part 204 and a tip 20 interacting part 206. Catheter insertion part 204 comprises a generally hollow cylindrical shape comprising a proximal blunt end 208, an external surface 210 and an interior lumen 212. Likewise, catheter 50 comprises an interior lumen surface 214.

Medially disposed along surface 210, adapter 200 comprises an annular shelf 216 adjacent a more distal bevelled edge 218 and a second hollow cylindrical section 220 comprising an outer surface 221 contiguous with edge 218 and forming a part of interacting part 206. Part 206 further comprises a blunt distal edge 222 and a lumen 224 which symmetrically communicates with lumen 212.

Surface 210 of insertion part 204 comprises a transverse diameter which causes a small displacement of lumen surface 214 as part 204 is inserted into catheter 50. Adapter 200 may be permanently affixed to catheter 50 by applying a bonding agent to surface 210 prior to insertion of part 204. After application of the bonding agent, part 204 is inserted until distal end 202 of catheter 50 is contiguous with shelf 216, after which the bonding agent is permitted to cure. The internal diameter of lumen 212 is large enough to permit passage of drive cable 30 without binding. The diameter of lumen 224 is large enough to permit assembly of parts connected to drive cable 30, also without binding.

Figure 6:
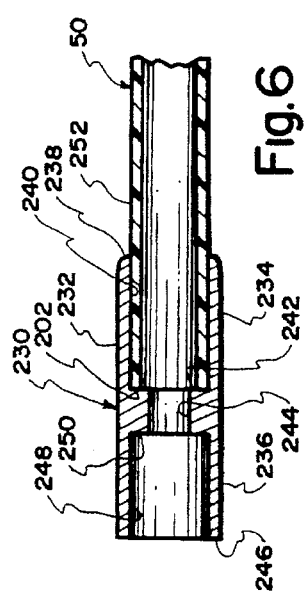
FIG. 6 is a section similar to the section of FIG. 5, but of a different catheter end attachment.

Referring to FIG. 6 a different adapter 230 comprises a substantially cylindrically shaped exterior surface 232 extending over a catheter connecting proximal section 234 and a distal section 236. Section 234 comprises a blunt proximal end 238, an interior lumen 240, and a medially disposed annular shelf 242 which decreases the size of lumen 240 to a smaller lumen 244. Distal section 236 comprises a blunt distal end 246, a lumen 248 which is open at end 246, a medially disposed interior shelf 250 which is contiguous with lumen 244 such that adapter 230 is hollow and comprises a medially disposed smallest lumen 244 comprising a transverse diameter large enough to pass drive cable 30 without binding. Catheter 50 comprises an outside surface 252.

The inside transverse diameter of lumen 240 causes the outside surface 252 of catheter 50 to be slightly compressed when catheter 50 is inserted into lumen 240. Adapter 230 may be permanently assembled and joined to catheter 50 by applying a bonding agent similar to bonding agents previously mentioned to surface 252. To assemble adapter 230 to catheter 50, catheter 50 is inserted into lumen 240 until distal end 202 of catheter 50 is contiguous with shelf 242 and the bonding agent is permitted to cure.

Figure 7:
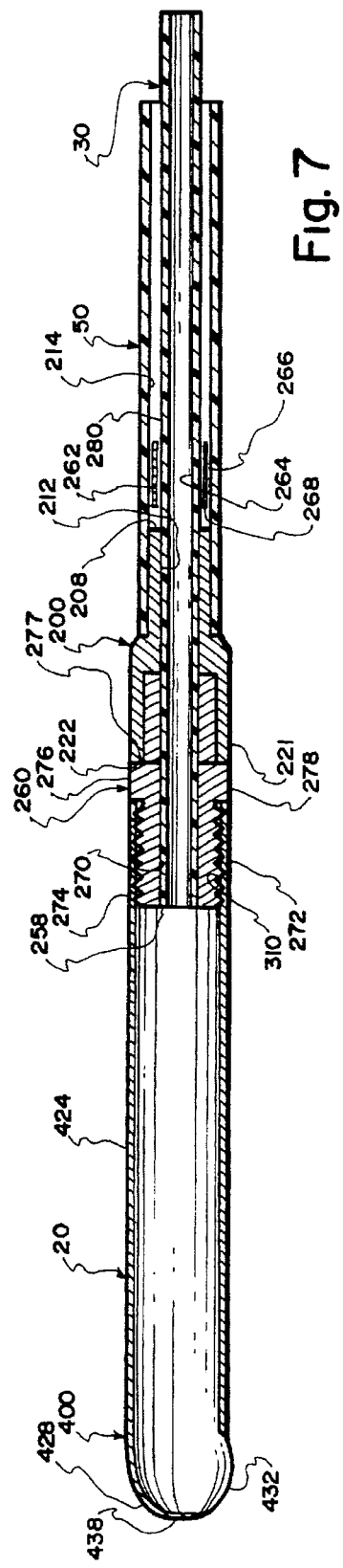
FIG. 7 is a cross section along lines 7—7 of FIG. 1 comprising an augering tip and a cable driver adapter connecting the tip to a drive cable.
Figure 8:
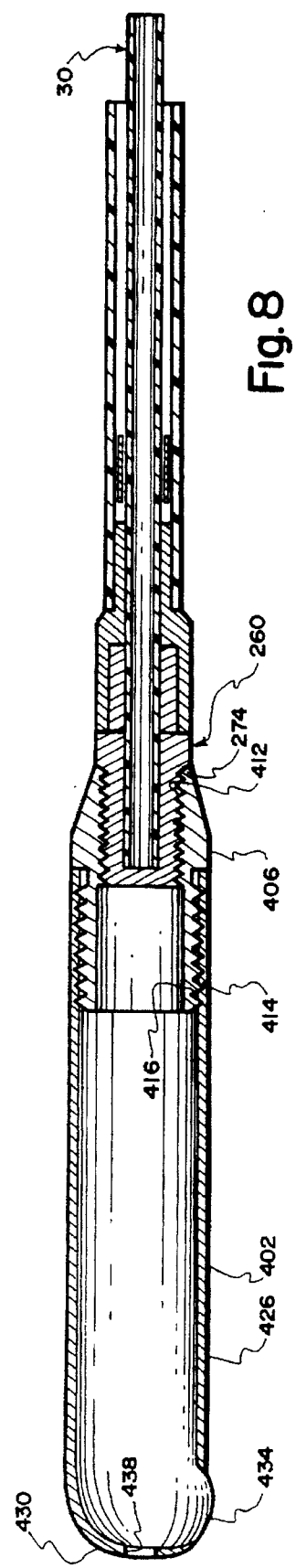
FIG. 8 is a cross section similar to FIG. 7, but comprising a larger diameter augering tip and an tip diameter adjusting connector interposed between the cable driver adapter and the larger diameter augering tip.

The relationship between distal ends of catheter 50 and associated adapter 200 and drive cable 30 and associated tip 20 connecting parts is best seen in cross section in FIG. 7. Attention is drawn to two parts disposed at and near the distal end 258 of drive cable 30, a threaded connector 260 disposed at end 258 and a retaining sleeve 262 proximally disposed from connector 260.

Retaining sleeve 262 comprises a hollow cylindrical shape having an inner surface 264, an outer surface 266, and a blunt distal end 268. Threaded connector 260 is a cylindrical piece having a hollow cylindrical core 270, a distal section 272 comprising a threaded outer surface 274, a more proximal section 276 comprising a proximal blunt end 277 and a smooth outer surface 278 having a diameter which is substantially the same diameter as surface 221 to form an atraumatic interface where the two surfaces 278 and 221 pass by tissue disposed inside an artery. Distally, drive cable 30 comprises an exterior surface 280 at sites of intersection between retaining sleeve 262 and connector 260.

As seen in FIG. 7, retaining sleeve 262 is attached by bonding or the like to drive cable 30 at a site proximally disposed from adapter 200. Outer surface 266 of retaining sleeve 262 comprises a diameter which is greater than the interior diameter of lumen 212 and less than lumen 214 such that drive cable 30 is free to move longitudinally inside catheter 50 until distal end 268 of retaining sleeve 262 is in contact with proximal blunt end 208 of adapter 200 which provides a stop, limiting further distal movement of drive cable 30.

Adapter 200 is affixed between connector 260 and retaining sleeve 262 to assure that drive cable 30 is moved as the distal end 202 of catheter is moved. One method of assembly is to first bond sleeve 262 to a predetermined site on drive cable 30, then to bond adapter 200 to catheter 50 and then to affix connecter 260 to drive cable 30. With adapter 200 so affixed between connector 260 and retaining sleeve 262 it is important that the proximal end of drive cable 30 be free to move longitudinally as in segment 160 to prevent binding by differential movement of catheter 50 and drive cable 30 as both are moved through a circuitous path of an artery.

Referring to FIG. 4, another instrument handle embodiment, a handle 40", is seen to comprise a majority of internal parts which are similar in form and function to those of handle 40, but few parts which permit variation in longitudinal position control of drive cable 30 relative to catheter 50 and a different placement for the motor on/off switch. Similar to handle 40, handle 40" comprises a housing 100" molded to enclose battery 102, motor 104, gears 106, 106' which interface motor 104 to drive cable drive channel 108, and mounting bracket 110 used to permanently affix catheter 50 to handle 40". Housing 100" is also made from rigid synthetic resinous material which is able to withstand sterilization procedures, such as gas or radiation sterilization.

Housing 100" comprises a pair of mounting shells, but as is true above in the description of housing 100, only a single mounting shell 112" will be described herein. In final assembly, mounting shell 112" is permanently joined to a mirror image shell by chemical, heat, ultrasound or other bonding techniques well known in the art to provide a durable, throw-away unit. Shell 112" may be formed by injection molding or vacuum forming techniques well known in the art.

As seen in FIG. 4 and as is true of housing 100, housing 100" provides a shape compatible for gripping with a single hand. Shell 112" comprises an enclosing side 114 orthogonally connected to a continuous perimeter 116" which surrounds half the space between side 114 and a like side on the mirror image shell when shell 112" and the mirror image shell are engaged. The mirror image shell comprises a perimeter, which is also a mirror image of perimeter 116" and which encloses the other half of the space between side 114 and a like side on the mirror image shell.

A substantially planar rim 118" is disposed parallel to side 114 but on a side of perimeter 116" opposite side 114. Perimeter 116" comprises a longest edge 120 which extends substantially along the length of handle 40" and is intended to provide a superiorly disposed thumb rest while in use. Medially disposed in edge 120 is a depression or recess 122 wherethrough a slidable mechanical device 124" is captured. The purpose and function of device 124" is described in detail hereafter.

Disposed at a right angle to edge 120 is a proximal edge 126. A semicircular slot 128 in combination with a similar slot in the perimeter of the mirror image shell provides access for a luer fitting 130, the purpose of which is also described hereafter. Inferiorly disposed and extending parallel to edge 120 from edge 126 is edge 132". Edge 132" extends in a straight line from edge 126 to a bend 134", although it is within the scope of the invention to provide scallops or grooves in edge 132" for more positive finger gripping of handle 40". At bend 134", edge 132" bends to form a bevelled edge segment 136" which may act as a gripping position for a forefinger. Medially disposed in segment 136" is a recess 137", the purpose for which is described in detail hereafter.

At a bend 138", segment 136" is joined to a distal edge 140 which is orthogonally joined at a bend 142 with edge 120 to complete perimeter 116". Medially disposed along a line which is parallel to edge 120 and which bisects slot 128, a catheter 50 exit slot 144 is disposed in edge 140. Additional detail regarding catheter 50 attachment and alignment is provided hereinafter.

As seen in FIG. 4, device 124" comprises an actuator 146 positioned to be normally operated by a thumb, a support bar 148, a memory biased member 150", and a coupling member 152. Member 152 is affixed to actuator 146 and captures support bar 148 and bias member 150" such that edge 120 is disposed between actuator 146 and bias member 150". Further, member 152 slides within a slot formed in part by recess 122 between at least a first proximal position and a second distal position.

In the embodiment seen in FIG. 4, bias member 150" is spring loaded to bias member 150" and support bar 148 away from edge 120 and comprises a distally extended arm section 290 which comprises a right angle bend at a distal end 292 and a yoke 294 which extends away from edge 120. A collar 296 is bonded or otherwise permanently affixed to drive cable 30 at a site medially disposed between the proximal end of catheter 50 and the distal end of tube 154. As seen in FIG. 4, yoke 294 comprises a pair of collars 296 capturing extensions, a proximal tine 298 and a distal tine 298', spaced apart to permit collar 296 and, therefore, drive cable 30 to rotate freely therebetween, yet tines 298 and 298' are sufficiently closely aligned to collar 296 to permit vernier control of longitudinal movement of drive cable 30 relative to catheter 50 as actuator 146 is moved longitudinally relative to handle 40".

In one embodiment of handle 40", a contactor similar to the contactor described above for handle 40 may disposed such that when actuator 146 is moved distally to the second position motor 104 is turned on and when actuator 146 is moved proximally to the first position motor 104 is turned off. In this manner, when drive cable 30 is moved distally relative to catheter 50, attached tip 20 is likewise moved and rotationally actuated by motor 104 at the same time.

Alternatively, in another embodiment of handle 40", a separate electrical switch 300 is disposed, as seen in FIG. 4, at recess 137" in segment 136". Recess 137" in shell 112" and a like recess in the mirror image shell provides a switch capturing slot for switch 300 when the two shells are joined. Switch 300 comprises a digital actuator 302, a spring loaded bias member 304, a support bar 306 and a coupling member 308. In combination, bias of member 304 and coupling of member 308 maintains member 304 in surface to surface contact with segment 136" as actuator 302 and coupling member 308 and, therefore, switch 300 is moved longitudinally from a first proximal position to a second distal position. As is the case of handle 40, an electrical contactor (not shown) makes an electrical contact with another contactor disposed on a medial side of edge 136" only at the second distal position. The electrical contacts and other electrical wiring are not shown in FIG. 4 as such is well known in the art and have been removed to provide greater detail and clarity of mechanical parts of handle 40".

Within handle 40", a cable drive system comprises device 124", battery 102, motor 104, gears 106 and 106', and cable drive channel 108. Battery 102 and motor 104 are aligned along edge 132" and confined by edge 132", sides 114 and the like side of mirror image shell, and brackets molded or formed into sides 114 and the like side of mirror image shell. The molded or formed brackets are not shown but molding and forming such brackets is widely practiced and well known in the handle molding art.

Rotary motor power from motor 104 is transferred through gear 106 to gear 106' and therefrom to cable drive channel 108. As disclosed above, cable drive channel 108 comprises a round hollow tube 154 captured in grooves in bearing parts 156 and 158 and like mirror image shell parts disposed at each end of cable drive channel 108. Medially disposed between bearing parts 156 and 158, tube 154 is squared by compressive techniques known in the art to form a segment 160 having a square cross section as described above for handle 40. Cable drive channel 108 is centrally aligned with luer fitting 130, gear 106', and catheter 50 mounting bracket 110. This alignment permits drive cable 30 to be interconnected with cable drive channel 108 and threaded through catheter 50 such that drive cable 30 rotates without binding within catheter 50. Further guide wire 162 can be threaded end-to-end through hollow drive cable 30, entering handle 40" through luer fitting 130.

A portion of drive cable 30 comprising section 164, seen in FIG. 3, is inserted into segment 160 such that at least a portion of section 164 is retained in segment 160 during all operational modes of instrument 10. As such, drive cable 30 is rotationally driven as cable drive channel 108 is rotated by action of motor 104 through gears 106 and 106'. In this embodiment, drive cable 30 is free to move longitudinally under control of actuator 146. However, to eliminate binding between drive cable 30 and catheter 50, a retaining sleeve 262, seen in FIG. 7, is not affixed to the distal end of drive cable 30 as disclosed for the embodiment of handle 40. Rather, drive cable 30 is left free at the distal end to move longitudinally within catheter 50. In this manner, as catheter 50 is moved through an artery, drive cable 30 is free on one end relative to catheter 50 to eliminate binding caused by differential movement of drive cable 30 and catheter 50.

Referring once more to FIG. 7, instrument 10 is seen to comprise a tip 20 having substantially the same external diameter as connector 260. Tip 20 comprises an internally disposed threaded surface 310 which screws to connect with the threaded outer surface 274 of connector 260. Direction of threads on surfaces 310 and 274 is counter to direction of rotation of drive cable 30, thereby causing tip 20 to only tighten upon rotation of drive cable 30 relative to frictional surfaces engaged by tip 20 in an artery.

As a further measure of safety, to assure a secure connection between connector 260 and tip 20, connector 260 is seen in FIGS. 9 and 9A to comprise a throat area 312 a flat 314 disposed on each side of connector 260. As such, flats 314 provide a connecting site for application of a wrench to hold connector 260 in place while tip 20 is securely tightened and affixed to connector 260.

A variety of tips 20 may be securely affixed to instrument 10 as different pathway generating needs warrant. Two versions of tips usable on instrument 10 comprise a smaller tip 400 and a larger tip 402 are seen in FIG. 9. As denoted by a mechanical assembly flow line 404, smaller tip 400 is directly affixed to connector 260 when used with instrument 10.

However, instrument 10 comprises a connector adapter 406 which is interposed between connector 260 and larger tip 402 when larger tip 402 is connected to drive cable 30. As seen in FIGS. 9 and 9B, connector adapter 406 comprises a throat area 408 and opposed wrench flats 410, similar in function but necessarily more widely separated than flats 314 of connector 260. Connector adapter 406 comprises a proximally disposed internal threaded surface 412, best seen in FIG. 8, which compatibly attaches to the threaded outer surface 274 of connector 260. Connector adapter 406 also comprises a distally disposed threaded surface 414 which compatibly accepts proximally disposed internally threaded surface 416 of larger tip 402. Direction Of threads on surfaces 414 and 416 are also counter to direction of rotation of drive cable 30. While two sizes of tips 400 and 402 and one connector adapter 406 have been described, it is within the scope of the invention to have more than two tip sizes and more than one size of connector adapters.

To affix tip 402 to drive line 30, connector adapter 406 is connected in place of tip 400 to connector 260 as indicated by mechanical assembly flow line 420, seen in FIG. 9. Tip 402 is connected to connector adapter 406 as indicated by a mechanical assembly flow line 422. In each case, a wrench is applied across available flats 314,410 to permit each connecting part to be tightly secured. Tip 402 is seen assembled to drive cable 30 in FIG. 8.

As atheroma and intimal and subintimal plague occurs in a wide variety of forms, thicknesses and hardnesses, it is important that a wide variety of tip 20 types be available for use with instrument 10. The following described tips provide an example of tips usable on instrument 10, but the examples provided should not be considered to limit the scope of the invention. Further, in a medical augering and dottering application which entails working to clear a pathway through an obstruction at a site deeply disposed within a patient and distantly disposed from an instrument 10 operator-appropriate consideration must be given to critical factors such as excised tissue retrieval and recovery, elimination of binding both between catheter 50 and drive cable 30 and between an exposed tip 20 and a pathway being cleared.

Such considerations are inherent in each tip 20 described hereafter. Referring again to FIGS. 7–9, tips 400 and 402 are each seen to comprise a hollow shaft 424 and 426, a distal rounded end 428 and 430, and a bulbous cutting blade 432 and 434, respectively. As tips 400 and 402 differ only in size, the following description solely references tip 400, but the description applies to tip 402 as well.

In transverse cross section, shaft 424 is substantially circular and comprises an internal threaded surface 310 as previously described. Distally, shaft 424 narrows to rounded end 428. As best seen in FIG. 9C, rounded end 428 comprises a slit 436 whereat bulbous cutting blade 432 is raised above the otherwise circular curvature of end 428. Blade 432 is sharpened to a knife-like edge and is separated from the otherwise circular curvature of end 428 by a space which passes material excised by blade 432 into the hollow of shaft 424. The length of shaft 424 provides storage for retrieval of material excised during a pathway cutting procedure. The bulbous prominence of blade 432 opens a pathway through each obstruction which is greater in transverse diameter than shaft 424, connector 260, adapter 200 and catheter 50 to obviate binding during augering excising and material removing operations.

As best seen in FIG. 9C, tip 400 also comprises a centrally disposed orifice 438 of sufficient transverse diameter that guide wire 162 passes through and resides without retarding rotation of drive cable 30 and tip 400. As seen in FIG. 7 a similar pathway is provided through drive cable 30 such that a path for guide wire 162 is available from luer fitting 130 to orifice 438. Such is the case for each tip disclosed herein unless specifically disclosed to be otherwise.

Referring to FIG. 14A, a tip 440 is seen to comprise an external silhouette which is similar to tip 400. Tip 440 comprises a shaft 442 which is shortened, but otherwise externally similar to shaft 424. Also tip 440 comprises a bulbous protruding blade 444 which is similar to blade 432 and a guide wire orifice 446 similar to orifice 438.

However, when viewed in cross section in FIG. 14A, tip 440 is seen to be different from tip 400. While it is within the skill level of one of ordinary skill in the art to make tip 440 releasibly attachable, tip 440 is seen to be permanently affixed to a drive cable extension 30' in FIG. 14A.

In addition to the features mentioned above, tip 440 comprises a centrally disposed hollow cylindrical channel 448 attached to orifice 446. Disposed about distal end 258 of drive cable 30, cable drive extension 30' comprises a distally disposed channel screw 450 and a tip connecting extension 452.

Orifice 446 and channel 448 comprise an inner surface which is permanently affixed by bonding or the like to drive cable extension 30' about tip connecting extension 452. So connected channel screw 450 and tip 440 rotate when driven by drive cable 30.

Permanently affixed by bonding or the like to the distal end 202 of catheter 50 is a tip adapter 454. Tip adapter 454 comprises a proximal sleeve 456, an annular mounting ring 458, and a distal tip insertion part 460. Part 460 comprises a bearing sleeve 462 and a scraper blade 464. Proximal sleeve 456 is a hollow cylindrical sleeve which is inserted into the distal end of catheter 50 and permanently affixed thereat in a manner similar to the attachment of adapter 200 to catheter 50 as earlier disclosed. Catheter 50 end 202 is abutted against a proximal face of annular ring 458 to affix the position of catheter 50 relative to tip adapter 454.

Distally disposed bearing sleeve 462 comprises an exterior surface 466 formed to provide a bearing surface for shaft 442 when tip 440 rotates. Extending distally from a portion of bearing surface 466, scraper blade 464 describes a shape which conforms to the minimal circular dimensions of the interior surface of tip 440. As scraper blade 464 is fixed in position relative to rotation of tip 440, blade 464 removes excised and entrapped material which is captured by tip 440 but would otherwise clog tip 440. The removed excised and entrapped material is urged proximally by channel screw 450 which rotates at the same angular rate as tip 440.

Drive cable extension 30' and tip adapter 454 may be made from metal, although both are preferably molded from rigid synthetic resinous material. Tip 440 is preferably made from stainless steel and may be made by methods well known and understood in art.

Another tissue excising tip 470 is seen in FIGS. 12 with a sectional portion of excising tip 470 being seen in FIG. 12A. Tip 470 comprises a shaft 472 and a substantially hemi-spherical distal end surface 474. Shaft 472 rotates in a manner similar to the rotation of shaft 424 seen in FIGS. 7 and 9C and is connected to drive cable 30 in the same manner as shaft 424 is connected to drive cable 30.

End surface 474 comprises a distally, centrally disposed orifice 480 and a plurality of convex grating edges 476 disposed upon rounded nose surface 474. Central orifice 480 provides a pathway for guide wire 162. As best seen in FIG. 12A, each convex grater blade 476 comprises a sharpened blade edge 478 which pares material encountered as tip 470 is rotated by drive cable 30. As each grater blade 476 comprises a convex, raised surface, material is excised above the tangential plane of surface 474. In particular, more proximally disposed grater blades 476, generally designated 482, are disposed above the exterior surface of shaft 472 and excise material to create a pathway greater than the transverse diameter of tip 470 to obviate binding within a newly created pathway. Tip 470 is preferably made from thin gauge stainless steel.

Another tip 490 is seen in FIGS. 13 and 13A. Tip 490 comprises an auger 492 having an exposed distal end 494. As seen in FIG. 13A, an end catheter interface 496 for auger 492 is permanently affixed to catheter 50 and disposed to enclose a large portion of auger 492. Interface 496 comprises a proximal catheter connecting end 498 and an auger enclosing end 500. Proximal catheter connecting end 498 comprises a hollow cylindrical insertion part 502 similar to insertion part 204 of adapter 200. Part 502 is permanently affixed to catheter 50 in the same manner part 204 is affixed to catheter 50. Distally disposed from part 502, auger enclosing end 500 comprises a hollow cylindrical sleeve 504. Sleeve 504 comprises a blunt open end 506 and a linear hollow cylindrical interior for enclosing a portion of auger 492 in freely rotating disposition.

Auger 492 comprises a through-bore 508 and an auger screw 510 pitched to rotate material into sleeve 504 when auger 492 is rotationally driven by drive cable 30. The transverse diameter of the enclosed portion of auger 492 disposed in sleeve 504 is substantially the same as the inner diameter of sleeve 504 with enough material removed from the exterior surface of the enclosed portion of auger 492 for uninhibited rotation. The portion of auger 492 which extends distally from sleeve 504 comprises a diameter greater than the exterior diameter of sleeve 504 such that a pathway created by rotating auger 492 and thereby excising matter from an obstructing atheroma is larger than sleeve 504 to obviate binding during pathway creation and tip 490 removal.

Auger 492 is connected to drive cable 30 by permanently affixing the distal end of drive cable 30 within through-bore 508. Auger 492 may be affixed to drive cable 30 by the use of bonding agents which are well known in the art. To retain auger 492 in a predetermined longitudinal position relative to sleeve 504, a retaining sleeve 262 (not shown in FIG. 13A, but found in FIGS. 7 and 15A) is affixed to drive cable 30 at a site proximal to catheter connecting end 498.

In addition to augering and excising tips, dottering tips, generally designated 520 with exemplary tips seen in FIGS. 15, 15A, 15B, and 15C are attached to instrument 10. Each dottering tip 520 is used to compress or otherwise move tissue to form a pathway rather than excising tissue from an obstructing site. A dottering tip 520 is particularly useful in forming a pathway through a relatively soft obstructing atheroma. To be used effectively, a dottering tip 520 must exert a force on the obstruction material transverse to the longitudinal axis of the pathway being formed.

The dottering tips 520 seen in FIGS. 15 and 15A–C are permanently affixed to drive cable 30. However, releasibly affixed dottering tips, attachable by the same methods described for attachment of tip 400 to connector 260 and therefrom to instrument 10 as earlier disclosed, are within the scope of the invention.

In the embodiment seen in FIG. 15, a dottering tip assembly 522 comprises generally designated dottering tip 520 connected to drive cable 30 and disposed at the distal end of catheter 50.

Seen in FIG. 15A, tip 520 comprises a bulbous distal end 534, a proximal cylindrical skirt 536, a proximal lumen 538 disposed along the longitudinal axis of drive cable 30 and a distal lumen 540 also disposed along the longitudinal axis of drive cable 30 but of reduced transverse diameter relative to the transverse diameter of lumen 538. Although only one general bulbous form is seen for tip 520 in FIGS. 15 and 15A–C, it should be apparent to one skilled in the art that a plurality of forms from more pointedly shaped tips to more obtusely shaped tips are within the scope of the invention.

In the embodiment seen in FIG. 15A, drive cable 30 is permanently attached to tip 520 by inserting drive cable 30 into lumen 538 until distal end 258 of drive cable 30 is stopped by the intersection of lumen 538 with lumen 540 and affixing drive cable thereat. Bonding or other like agents may be used to permanently affix tip 520 to drive cable 30. So disposed, lumen 540 is aligned with the hollow core of drive cable 30 to facilitate passage of guide wire 162. It should be noted that, under some circumstances, it may be best to impede guide wire 162 from exiting a dottering tip. In that circumstance a dottering tip which does not comprise lumen 540 is attached to instrument 10 and used.

When dottering tip 520 is attached to drive cable 30, skirt 536 slips loosely over the distal end of catheter 30 to be freely rotated by drive cable 30. However, though such movement of tip 520 and skirt 536 is free and unimpeded, such movement is may or may not be smooth. While tip 520 is seen to be symmetrical in FIG. 15A, it is preferable under some circumstances to use an asymmetric or imbalanced tip.

Referring to FIG. 15B, a specific form of dottering head 520, dottering head 550, is seen in magnified format to comprise an asymmetric or imbalanced weight distribution relative to the axis of rotation of dottering tip 550. Tip 550 comprises a weighted part 552 disposed off-rotational axis within tip 550. Part 552 comprises a mass and density which causes tip 550 to dotter or vibrate transversely when rotationally driven at a predetermined speed by motor 104.

A dottering tip 560 comprising an asymmetric structure is seen in FIG. 15C. Similar to the asymmetric weight distribution of tip 550, tip 560 comprises a bulged section 562, magnified for clarity and understanding, on one side. Bulged section 562 causes tip 560 to vibrate transversely or dotter in a manner similar to the dottering of tip 550. Such dottering of tips 550 and 560 compressively form a pathway through atheroma without excising tissue and therefore requiring retrieval of excised tissue.

In circumstances where an obstruction is relatively thin or when it is desired to create a "starter" hole in an obstruction formed of hardened tissue, it is sometimes desirable to drill into or through the obstruction with a more positively drilling and sharper auger tip. An example of such a tip 600 is seen in FIGS. 10 and 10A. Tip 600 is an extendable and retractable tip, normally retracted while catheter 50 is delivered to an obstructed site and retrieved from the site.

Tip 600 comprises a relatively small, but blunt distal tip 602 and an auger bit 604 extending proximally from tip 602. Auger bit 604 comprises a distally disposed conical section 606 contiguously connected to a more proximally disposed cylindrical section 608 and a common outer surface 610. Surface 610 comprises at least one helical groove 612 which is continuous across sections 606 and 608. Each at least one groove 612 comprises a cutting edge 614 disposed on the distal side of groove 612 such that when auger bit is rotated in the direction indicated by arrow 616, material contacting surface 610 is excised and trapped within groove 612.

Better seen in FIG. 14A, auger bit 604 is directly affixed to drive cable 30. Auger bit 604 comprises a distally extending longitudinal blind bore 618 through a proximal face 620 of bit 604.

To assembly tip 600 to drive cable 30, drive cable 30 is cut to a predetermined length. The length of drive cable 30 permissively allows tip 600 to be retracted within catheter 50 or to be extended distally out of catheter 50 in cutting orientation. The position of tip 600 is longitudinally adjusted relative to end 202 of catheter 50 by selective movement of actuator 146 of handle 40" seen in FIG. 4. Longitudinal extension of tip 600 relative to catheter 50 is limited to assure that cylindrical section 608 remains disposed within catheter 50 at all times. The transverse diameter of cylindrical section 608 is determined to assure that material previously captured in groove 612 and urged into the portion of surface 610 enclosed by catheter 50 is urged proximally due to an interface with the inner surface of lumen 214 of catheter 50 while auger bit is rotating and, thereat, surrounded and captured when auger bit 604 is stationary. Tip 600 is preferably made from medical grade stainless steel.

When tip 600 is disposed in an artery 622 at an obstructing atheroma site 624 as seen in FIG. 10A, auger bit 604 is engaged with the atheroma at site 624 and rotationally driven in the direction of arrow 616 to excise material along surface 610. Material is excised by cutting edge 614 and forced into groove 612 by combined forces of tip 600 and material remaining at site 624. As auger bit 604 turns, the excised material is maintained in groove 612 and forced proximally toward and into catheter 30. When a pathway has been cleared through or a "starter" hole has been drilled into an obstructed site, tip 600 is retracted into catheter 50 and retrieved from artery 622 along with excised material captured within each groove 612.

Reference is now made to FIG. 11 wherein a spirally configured cutting tip 700 is seen. Spiral cutting tip 700 comprises a drive cable connecting structure which is similar to tip 440 (see FIGS. 14 and 14A). Tip 700 comprises a shaft 702 which like shaft 442 is shortened and a blade which is proximally disposed at substantially the same transverse exterior diameter as that of shaft 702. Tip 700 also comprises a guide wire orifice 706 similar to orifice 446.

While it is within the scope of the invention and the skill level of one of ordinary skill in the art to make tip 700 releasibly attachable to drive cable 30, tip 700 and drive cable extension 30' is seen to be permanently affixed to a drive cable 30 in FIG. 11B. As seen therein, tip 700 comprises a centrally disposed hollow cylindrical channel 708 attached to orifice 706. Channel 708 comprises a blunt end 710 disposed in substantially the same transverse plane as a proximal end 712 of shaft 702. Channel 708 comprises a transverse diameter which is permissive to an enclosing attachment by hollow drive cable 30. As such, tip 700 is connected to drive cable 30 by insertion of channel 708 into the distal end of drive cable 30 and thereat permanently affixed. Channel 708 may be affixed by bonding or other method of safe attachment known and used in the art.

Permanently affixed at the distal end 202 of catheter 50 is a tip adapter 714. Tip adapter 714 comprises a proximal sleeve 716, an annular mounting ring 718, and a distal tip insertion part 720. Part 720 comprises a bearing sleeve 722. Proximal sleeve 716 is a hollow cylindrical sleeve which is inserted into the distal end of catheter 50 and permanently affixed thereat in a manner similar to the attachment of adapter 200 (see FIG. 5). Catheter 50 end 202 is abutted against a proximal face of annular ring 718 to affix the position of catheter 50 relative to tip adapter 714. Distally disposed bearing sleeve 722 comprises an exterior surface 726 formed to provide a bearing surface for shaft 702 when tip 700 is rotating. While shaft 702 is substantially transversely circular for rotation upon surface 726, tip 700 comprises a rounded nose surface 728 which is distally transversely spirally formed to better expose a lateral butting blade 730. As seen in combination in FIGS. 11 and 11A, an end of the circular portion of shaft 702 is marked by line 732. From line 732, a portion of surface 728 is medially depressed to a contiguous connection with a spiral line 734. From spiral line 734 to orifice 706, surface 728 is so defined such that any plane distal to line 734 and parallel to line 734 intersects tip 700 in a line which is also a spiral. As such surface 728 defines an medial opening below blade 730 wherethrough excised tissue is captured within tip 700 for subsequent retrieval when tip 700 is withdrawn from an excising site. Tip 700 is preferably made by a coining process from stainless steel, such coining processes are well known and understood in art.

A combined augering and dottering tip 750 is seen in FIGS. 17 and 17A. So combined tip 750 provides a steering and coring end for catheter 50 and drive cable 30, not seen in FIGS. 17 and 17A as only the distal end of tip 750 is provided for detail and clarity of presentation and connections to catheter 50 and drive cable 30 are substantially the same as described for tip 400 above and as seen in FIG. 9. Tip 750 is preferably a replaceable tip as 400 is replaceable.

As seen in FIG. 17, tip 750 comprises a proximal augering segment 752, with a securely affixed shaft 754 extending distally from segment 752. Securely attached to the distal end 756 of shaft 754 is a dottering tip 758. Dottering tip 758 is similar in form and dottering function to dottering tip 520, seen in FIG. 15. However, rather than being rotated as an individual part as tip 520 rotates about catheter 50 as driven by drive cable 30, dottering tip 758 rotates as driven by augering segment 752, which is driven as tip 400 is driven by cable 30.

Best seen in FIG. 17A, dottering tip 758 comprises a bulbous distal end 760, a proximal lumen 762 disposed along the longitudinal axis of shaft 754 and a distal lumen 764 also disposed along the longitudinal axis of shaft 754 but of reduced transverse diameter relative to the transverse diameter of lumen 762. Although only one general bulbous form is seen for dottering tip 758 in FIGS. 17 and 17A, it should be apparent to one skilled in the art that a plurality of main forms from more pointedly shaped tips to more obtusely shaped tips are within the scope of the invention and that the off-balancing shapes and configurations of FIGS. 15B and 15C apply to dottering tip 758 as well.

As seen in FIG. 17A, shaft 754 is attached to dottering tip 758 by inserting shaft 754 into lumen 762 until a distal end 766 of shaft 754 is impeded by the intersection of lumen 764 with lumen 762 and permanently affixed thereat. Bonding or other like agents may be used to permanently affix dottering tip 758 to shaft 754. So disposed, lumen 762 is aligned with a hollow core 768 of shaft 754, which is proximally aligned with drive cable 30, to facilitate passage of guidewire 162. It should be noted that, under some circumstances, it may be best to impede guidewire 162 from exiting a dottering tip. In that circumstance a dottering tip which does not comprise lumen 764 is attached to instrument 10 and used.

Segment 752 is seen to comprise an external silhouette which is similar to tip 400. Segment 752 comprises a shaft 770 which is similar to shaft 424 of tip 400. Also segment 752 comprises a bulbous protruding blade 772 which is similar to blade 432.

However, when viewed in cross section in FIG. 17A, segment 752 comprises a connection to shaft 754 which is different from tip 400. Segment 752 comprises a distal orifice 774 through which shaft 754 is inserted and affixed to segment 752. Segment 752 also comprises a centrally disposed hollow cylindrical channel 776 attached to orifice 774. Orifice 774 and channel 776 comprise an inner surface 778 which is permanently affixed by bonding or the like to shaft 754 about a medially inserted segment 780 of shaft 754. So connected, both shaft 754 and dottering tip 758 rotate when driven by segment 752 which is driven by drive cable 30 as previously described for tip 400.

Shaft 754 may be made from a resilient metal such as spring steel, although both it is preferably made from extruded resilient synthetic resinous material. Dottering tip 758 is preferably made from the same materials and methods used for tip 520. Segment 752 is preferably made from the same materials and methods used for tip 440. The combination of augering segment 752 and dottering tip 758 on the same tip 750 provides a tip which facilely dotters through a totally or nearly totally obstructed vessel and which then cores and removes a larger diameter portion of the obstruction without removing and replacing tip 750. Also, dottering tip 758 impedes action of the antegrade coring and material excising blade 772 from harmful contact with the vessel wall adding a further element of safety.

Figure 16:
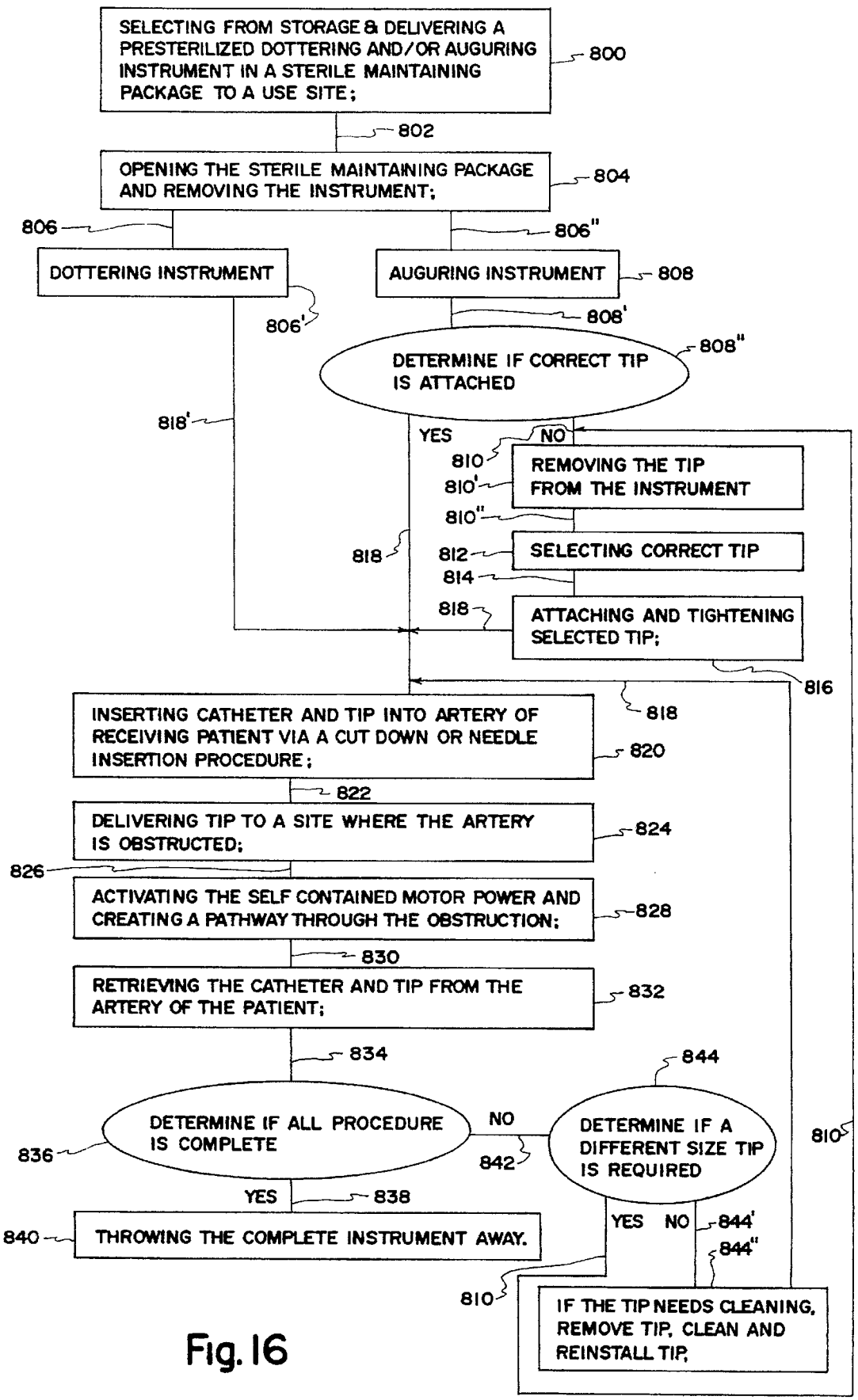
FIG. 16 is a flow diagram describing a method of use of a disposable augering and dottering instrument.

Reference is now made to FIG. 16 which provides a flow diagram illustrating a method for using a selectively chosen instrument 10. Before use, a plurality of instruments 10 are available from storage or directly from a vendor as a presterilized, prepackaged, self-contained augering and/or dottering instrument which is immediately ready for use when a difficult to traverse artery obstruction is encountered in an atherectomy procedure. As indicated in function block 800, a particular instrument 10 is selected from shelf storage and delivered to an operating site.

A sterilized package is not shown in the drawings. However, such packages are well known and widely used in the medical packaging art. A method of sterilization is also not defined. Methods of sterilizing packages such as gas and radiation sterilization are well known in the art.

When an obstruction for which an augering and dottering instrument 10 is required, a presterilized augering and dottering instrument 10 is selected from storage for immediate use as described in functional block 800. Via flow line 802, the next in line operation is opening the sterile maintaining package containing the selected instrument 10 as defined in functional block 804. When the selected instrument 10 comprises a dottering tip, generally designated above as 520, flow line 806 is taken to dottering instrument pathway block 806'. If the selected instrument 10 comprises an augering tip, designated by a plurality of numbers comprising 400, 440, 470, 490, 600, and 700, above, flow line 806" is taken to augering instrument pathway block 808. For simplicity in describing FIG. 16, the augering tip will be referenced as tip 400, although it should be understood that all augering tips and combination augering and dottering tips within the scope of this invention are referenced thereby. From block 808, flow path 808' is followed to a decision block 808".

At decision block 808", a determination is made as to whether or not a correct augering tip 400 is affixed to the selected instrument 10. If the answer is "no", flow line 810 is followed to function block 810' whereat a the resident augering tip 400 is removed from the selected instrument 10. From block 810', flow line 810" is followed to a block 812 in which a correct augering tip 400 is selected. From block 812, flow line 814 leads to block 816 where the correct augering tip 400 is attached and tightened per block 816. From function block 816 flow line 818 leads to function block 820. If the answer at decision block 808" was "yes" or if a dottering instrument 520 is used defining a pathway through block 806', flow line 818 is also followed to function block 820.

At function block 820, catheter 50 and affixed tip 20, which is either augering tip 400 or dottering tip 520, of instrument 10 is inserted into an artery of a patient via a medically approved cut down or needle insertion procedure, both of which are well known and widely used in the catheterization art. After tip 20 and catheter 50 are inserted, flow line 822 is followed to function block 824. Function at block 824 delivers tip 20 to a targeted obstructed site. Once tip 20 is at the obstructed site, flow line 826 is followed to block 828. At block 828, motor 104 is activated under power of battery 102 to drive drive cable 30 to rotate tip 20 to create a pathway through the obstruction.

Once a pathway through the obstruction is cleared for blood flow and traverse of other atherectomy devices, flow line 830 is followed to function block 832 which defines retrieving catheter 50 and tip 20 from the artery of the patient.

From block 832, flow line 834 is taken to decision block 836 wherein a determination is made as to whether or not all instrument 10 procedures have been completed. If the answer is "yes", flow line 838 is followed to function block 840. Block 840 requires safe, medical disposal of instrument 10 as a throw away instrument.

If the answer to the question raised at decision block 836 is "no", flow line 842 is taken to decision block 844. At decision block 844, a question is raised for determination as to whether or not a different size tip 20 is required. If a different size tip 20 is required, flow path 810 is taken to block 810' to follow the pathway through block 810', described above. If the same tip 20 is to be used, flow path 844' leads to block 844". At block 844", if tip 20 requires cleaning, cleaning is performed according to medically approved standards. Once an acceptably clean tip 20 is ready, flow path 818 returns operation to block 820 to perform another augering and dottering cycle.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed and desired to be secured by Letters Patent is:

1. A dottering tip which is used in conjunction with a catheter and a rotary drive cable to clear a pathway in an artery to completely constructed artery initially impassable by other atherectomy devices, said dottering tip comprising:

a connector for connecting the tip to the drive cable;

a symmetrically bulbous distal end comprising an asymmetric distribution of weight about the longitudinal axis of the tip to enhance oscillation of the tip without electrosurgical phenomenon.

2. A combined two segment antegrade coring and dottering tip which is used in conjunction with a catheter and a rotary drive cable to clear a pathway in a severely to completely obstructed artery initially impassable by other atherectomy devices, said combined antegrade coring and dottering tip comprising:

a proximally disposed antegrade coring and material excising segment comprising a first connector for connecting to the drive cable;

a flexible shaft comprising a second connector for connecting to the coring and material excising segment, a hollow core disposed for passing a guide wire, and an advancer for extending the flexible shaft distally relative to the proximal coring and material excising segment;

a bulbous dottering segment disposed and securely affixed at the distal end of the flexible shaft.

3. A combined two segment antegrade coring and dottering tip according to claim 2 wherein the first connector comprises a coupling mechanism for manually releasibly connecting the drive cable to the antegrade coring and material excising segment.

4. A combined two segment antegrade coring and dottering tip according to claim 2 wherein the bulbous dottering tip comprises an asymmetric distribution of mass about the longitudinal axis of the bulbous dottering tip.

5. A combined two segment antegrade coring and dottering tip according to claim 2 wherein the bulbous dottering tip comprises a passageway for passing the guide wire from the hollow core of the flexible shaft through the bulbous dottering tip.

6. A method for clearing a pathway in a severely to completely obstructed artery, said combination comprising:

removing from storage a self-contained sterilized instrument in a protective package, said instrument comprising an augering and dottering tip drive cable enclosed within a shielding catheter, a handle comprising a housing and, disposed within the housing, a motor and a motor power source and a driver for driving the drive cable from the motor, and a coupler for releasibly attaching predetermined augering and dottering tips to a distal end of the instrument;

removing the instrument from the protective package;

selecting and attaching a preselected tip to the instrument;

inserting the tip and distal position of the catheter into an artery of a patient;

delivering the tip to the site of the obstruction in the artery;

actuating the motor;

clearing a tip and catheter passable pathway through the completely constructed artery;

removing the instrument from the pathway and from the artery of the patient;

throwing away the instrument.

7. A method for clearing an obstructed site within an artery which is impeding distal movement of a guide wire comprising the steps of:

providing a catheter comprising a dottering tip on a distal end of said catheter;

threading said dottering tip and said catheter along said guide wire until the tip reaches the site of the obstruction;

rotating said dottering tip while moving the tip distally until the obstructed site is cleared;

displacing the guide wire through the cleared site;

removing the catheter and dottering tip from the artery.

8. A tool which is used in conjunction with a catheter and a rotary drive cable to clear a pathway in a severely to completely obstructed artery initially impassable other atherectomy devices, said tool comprising:

a connector for connecting the tool to the drive cable;

a dottering portion comprising a bulbous distal end comprising an asymmetric distribution of mass about the longitudinal axis of the tip;

an augering portion for excising matter from the inside of an artery comprising a cutting edge having a cutting radius which is greater than the traverse diameter of the rest of augering portion;

the dottering portion being juxtaposed the augering portion.

* * * * *